(12) United States Patent
Iding et al.

(10) Patent No.: US 10,858,324 B2
(45) Date of Patent: Dec. 8, 2020

(54) PROCESSES FOR THE PREPARATION OF PYRIMIDINYLCYCLOPENTANE COMPOUNDS

(71) Applicant: GENENTECH, INC., South San Francisco, CA (US)

(72) Inventors: Hans Iding, Rheinfelden (CH); Reinhard Reents, Muenchenstein (CH); Michelangelo Scalone, Birsfelden (CH); Francis Gosselin, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 16/555,842

(22) Filed: Aug. 29, 2019

(65) Prior Publication Data

US 2020/0062717 A1    Feb. 27, 2020

Related U.S. Application Data

(62) Division of application No. 15/827,985, filed on Nov. 30, 2017, now Pat. No. 10,435,378, which is a division of application No. 15/036,741, filed as application No. PCT/US2014/065567 on Nov. 13, 2014, now Pat. No. 9,862,689.

(30) Foreign Application Priority Data

Nov. 15, 2013    (EP) .................................. 13193030

(51) Int. Cl.
*A61K 31/517* (2006.01)
*C07D 239/70* (2006.01)
*C07C 269/06* (2006.01)
*C07C 271/22* (2006.01)
*C12P 17/16* (2006.01)

(52) U.S. Cl.
CPC .......... *C07D 239/70* (2013.01); *C07C 269/06* (2013.01); *C07C 271/22* (2013.01); *C12P 17/165* (2013.01); *C07B 2200/07* (2013.01)

(58) Field of Classification Search
CPC ............................ A61K 31/517; C07D 403/04
USPC ....................................... 514/252.16; 544/253
See application file for complete search history.

(56) References Cited

U.S. PATENT DOCUMENTS

| | | | |
|---|---|---|---|
| 8,063,050 B2 | 11/2011 | Mitchell et al. | |
| 8,853,199 B2 | 10/2014 | Mitchell et al. | |
| 9,278,917 B2 | 3/2016 | Remarchuk et al. | |
| 9,309,204 B2 | 4/2016 | Lane et al. | |
| 9,315,471 B2 * | 4/2016 | Babu .................. | C07D 403/04 |
| 9,359,340 B2 | 6/2016 | Mitchell et al. | |
| 9,416,110 B2 | 8/2016 | Askin et al. | |
| 9,676,730 B2 | 6/2017 | Askin et al. | |
| 9,790,190 B2 | 10/2017 | Lane et al. | |
| 9,862,689 B2 | 1/2018 | Iding et al. | |
| 10,435,378 B2 | 10/2019 | Iding et al. | |
| 2013/0059859 A1 | 3/2013 | Punnoose | |
| 2016/0235754 A1 | 8/2016 | Mitchell et al. | |
| 2017/0247338 A1 | 8/2017 | Gosselin et al. | |
| 2018/0169099 A1 | 6/2018 | Mitchhell et al. | |

FOREIGN PATENT DOCUMENTS

| | | |
|---|---|---|
| WO | 2008006032 A1 | 1/2008 |
| WO | 2008006040 A1 | 1/2008 |
| WO | 2009089453 A1 | 7/2009 |
| WO | 2009089459 A1 | 7/2009 |
| WO | 2012135750 A1 | 10/2012 |
| WO | 2012135781 A1 | 10/2012 |
| WO | 2013173779 A1 | 11/2013 |
| WO | 2013173784 A1 | 11/2013 |
| WO | 2013173811 A1 | 11/2013 |

OTHER PUBLICATIONS

U.S. Appl. No. 11/773,949, now U.S. Pat. No. 8,063,050.
U.S. Appl. No. 13/272,079, now U.S. Pat. No. 8,853,199.
U.S. Appl. No. 14/458,062, now U.S. Pat. No. 9,359,340.
U.S. Appl. No. 15/140,874, 2016-0235754.
U.S. Appl. No. 15/670,874, 2018-0169099.
U.S. Appl. No. 14/401,091, now U.S. Pat. No. 9,309,204.
U.S. Appl. No. 14/401,087, now U.S. Pat. No. 9,416,110.
U.S. Appl. No. 15/204,715, now U.S. Pat. No. 9,676,730.
U.S. Appl. No. 15/593,064, now U.S. Pat. No. 9,790,190.
U.S. Appl. No. 15/782,620.

(Continued)

*Primary Examiner* — Jeffrey H Murray
(74) *Attorney, Agent, or Firm* — Viksnins Harris Padys Malen LLP

(57) ABSTRACT

The present invention relates to a process for the preparation of a compound of formula (I)

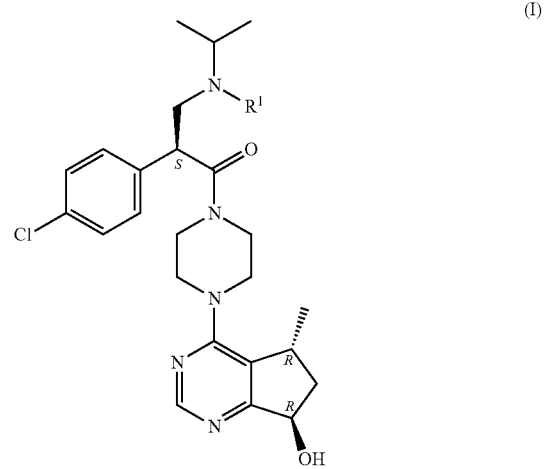

wherein $R^1$ is as defined herein, which is useful as an intermediate in the preparation of active pharmaceutical compounds.

12 Claims, No Drawings

(56) References Cited

OTHER PUBLICATIONS

U.S. Appl. No. 14/401,095, now U.S. Pat. No. 9,278,917.
U.S. Appl. No. 14/401,089, now U.S. Pat. No. 9,315,471.
U.S. Appl. No. 15/514,188, 2017-0247338.
Bastin, Richard J, et al., "Salt Selection and Optimisation Procedures for Pharmaceutical New Chemical Entities", Organic Process Research & Development 4, 427-435 (2000).
Blake, James F., et al., "Discovery and Preclinical Pharmacology of a Selective ATP-Competitive Akt Inhibitor (GDC-0068) for the Treatment of Human Tumors", Journal of Medicinal Chemistry 55, 8110-8127 (2012).
Chakravarty, P, et al., "Identification of a potential conformationally disordered mesophase in a small molecule: experimental and computational approaches", Mol Pharmaceutics 10(8), 2809-2822 (2013).
Elaridi, J., et al., "An enantioselective synthesis of B2-amino acid derivatives", Tetrahedron: Asymmetry, vol. 16, p. 1309-1319 (2005).
Lane, Jonathan W., et al., "Synthesis of Akt Inhibitor Ipatasertib. Part 1. Route Scouting and Early Process Development of a Challenging Cyclopentylpyrimidine Intermediate", Org. Process Res. Dev. 18, 1641-1651 (2014).
Liang, P, et al., "Prelog and anti-Prelog stereoselectivity of two ketoreductases from Candida glabrata", Biotechnol Lett 35, 1469-1473 (2013).
Patent Cooperation Treaty, International Searching Authority, Search Report and Written Opinion for PCT/US2014/65567, 9 pages, Jan. 27, 2015.
Remarchuk, T, et al., "An Efficient Catalytic Asymmetric Synthesis of a β2-Amino Acid on Multikilogram Scale", Organic Process Research & Development 18, 135-141 (2014).
Remarchuk, Travis, et al., "Synthesis of Akt Inhibitor Ipatasertib. Part 2. Total Synthesis and First Kilogram Scale-up", Organic Process Research and Development 18, 1652-1666 (2014).
Stahl, PH, et al., "Handbook of Pharmaceutical Salts", Handbook of Pharmaceutical Salts, 1st edition (2002).

* cited by examiner

PROCESSES FOR THE PREPARATION OF PYRIMIDINYLCYCLOPENTANE COMPOUNDS

RELATED APPLICATIONS

This application is a divisional application of U.S. application Ser. No. 15/827,985, filed Nov. 30, 2017, which is a divisional application of U.S. application Ser. No. 15/036,741, filed May 13, 2016, now issued as U.S. Pat. No. 9,862,689 which is a 371 national stage application of International Patent Application Number PCT/US2014/065567, filed Nov. 13, 2014, which claims priority to European Patent Application Number 13193030.7, filed Nov. 15, 2013, all of which are incorporated herein by reference in their entirety.

FIELD OF THE INVENTION

The present invention relates to processes for the preparation of pyrimidinylcyclopentane compounds which are useful as intermediates in the preparation of AKT protein kinase inhibitors with therapeutic activity against diseases such as cancer.

BACKGROUND OF THE INVENTION

The Protein Kinase B/Akt enzymes are a group of serine/threonine kinases that are overexpressed in certain human tumors. International Patent Application WO 2008/006040 and U.S. Pat. No. 8,063,050 discuss a number of inhibitors of AKT, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib, GDC-0068), which is being investigated in clinical trials for the treatment of various cancers.

While processes described in WO 2008/006040 and U.S. Pat. No. 8,063,050 are useful in providing hydroxylated cyclopenta[d]pyrimidine compounds as AKT protein kinase inhibitors, alternative or improved processes are needed, including for large scale manufacturing of these compounds.

SUMMARY OF THE INVENTION

The present invention provides processes for the preparation of a compound of formula (I)

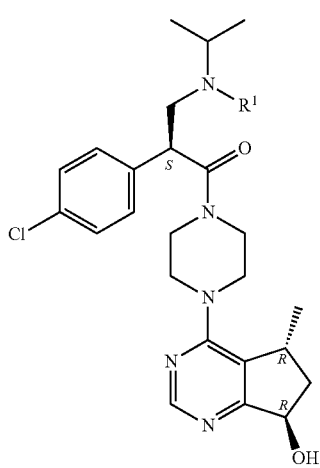

or salts thereof, which comprise the coupling reaction of a compound of formula (II)

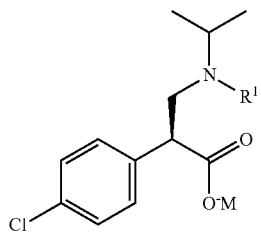

with a compound of formula (III)

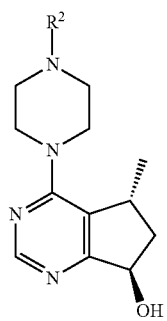

wherein $R^1$, $R^2$ and M are as described herein.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "stereoisomer" denotes a compound that possesses identical molecular connectivity and bond multiplicity, but which differs in the arrangement of its atoms in space.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The term "enantiomers" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "diastereomeric excess" (de) denotes the diastereomeric purity, i.e. (diastereomer A−diastereomer B)/(diastereomer A+diastereomer B) (in area %).

The term "enantiomeric excess" (ee) denotes the enantiomeric purity, i.e. (enantiomer A−enantiomer B)/(enantiomer A+enantiomer B) (in area %).

The term "halo", and "halogen" are used interchangeably herein and denote fluoro, chloro, bromo, or iodo.

The term "halide" denotes a halogen ion, particularly fluoride, chloride, bromide or iodide.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "alkenyl" denotes a monovalent linear or branched hydrocarbon group of 2 to 7 carbon atoms with at least one double bond. In particular embodiments, alkenyl has 2 to 4 carbon atoms with at least one double bond. Examples of alkenyl include ethenyl, propenyl, prop-2-enyl, isopropenyl, n-butenyl, and iso-butenyl.

The term "alkynyl" denotes a monovalent linear or branched saturated hydrocarbon group of 2 to 7 carbon atoms comprising one, two or three triple bonds. In particular embodiments alkynyl has from 2 to 4 carbon atoms comprising one or two triple bonds. Examples of alkynyl include ethynyl, propynyl, and n-butynyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

The term "aryl" denotes a monovalent aromatic carbocyclic mono- or bicyclic ring system comprising 6 to 10 carbon ring atoms. Examples of aryl moieties include phenyl and naphthyl. Particular aryl is phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

"Leaving group" refers to a portion of a first reactant in a chemical reaction that is displaced from the first reactant in the chemical reaction. Examples of leaving groups include, but are not limited to, hydrogen, halogen, hydroxyl groups, sulfhydryl groups, amino groups (for example —NRR, wherein R is independently alkyl, alkenyl, alkynyl, cycloalkyl, phenyl or heterocyclyl and R is independently optionally substituted), silyl groups (for example —SiRRR, wherein R is independently alkyl, alkenyl, alkynyl, cycloalkyl, phenyl or heterocyclyl and R is independently optionally substituted), —N(R)OR (wherein R is independently alkyl, alkenyl, alkynyl, cycloalkyl, phenyl or heterocyclyl and R is independently optionally substituted), alkoxy groups (for example —OR, wherein R is independently alkyl, alkenyl, alkynyl, cycloalkyl, phenyl or heterocyclyl and R is independently optionally substituted), thiol groups (for example —SR, wherein R is independently alkyl, alkenyl, alkynyl, cycloalkyl, phenyl or heterocyclyl and R is independently optionally substituted), sulfonyloxy groups (for example —OS(O)1-2R, wherein R is independently alkyl, alkenyl, alkynyl, cycloalkyl, phenyl or heterocyclyl and R is independently optionally substituted), sulfamate groups (for example —OS(O)1-2NRR, wherein R is independently alkyl, alkenyl, alkynyl, cycloalkyl, phenyl or heterocyclyl and R is independently optionally substituted), carbamate groups (for example —OC(O)2NRR, wherein R is independently alkyl, alkenyl, alkynyl, cycloalkyl, phenyl or heterocyclyl and R is independently optionally substituted), and carbonate groups (for example —OC(O)2R, wherein R is independently alkyl, alkenyl, alkynyl, cycloalkyl, phenyl or heterocyclyl and R is independently optionally substituted). Example carbonate groups include tert-butyl carbonate.

Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)). Other examples of leaving groups include substituted and unsubstituted amino groups, such as amino, alkylamino, dialkylamino, hydroxylamino, alkoxylamino, N-alkyl-N-alkoxyamino, acylamino, sulfonylamino, t-butyloxand the like.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular example of an amino-protecting group is tert-butoxycarbonyl (BOC).

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide. Particular deprotecting reagent is hydrochloric acid.

The term "buffer" denotes an excipient, which stabilizes the pH of a preparation. Suitable buffers are well known in the art and can be found in the literature. Particular pharmaceutically acceptable buffers comprise histidine-buffers, arginine-buffers, citrate-buffers, succinate-buffers, acetate-buffers and phosphate-buffers. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The term "alkali metal" refers to the chemical elements of Group 1 of the periodic table, i.e. lithium (Li), sodium (Na), potassium (K), rubidium (Rb), caesium (Cs), and francium (Fr). Particular examples of alkali metals are Li, Na and K, most particularly Na.

The term "alkaline earth metal" refers to the chemical elements of Group 2 of the periodic table, i.e. beryllium (Be), magnesium (Mg), calcium (Ca), strontium (Sr), barium (Ba), and radium (Ra). Particular examples of alkaline earth metals are Mg and Ca.

The term "transition metal" denotes chemical elements whose atoms have an incomplete d sub-shell.

ABBREVIATIONS

Ac acetyl
AcOH acetic acid
AN acetonitrile
BINAP 2,2'-Bis(diphenylphosphino)-1,1'-binaphthyl
BINAPHANE 1,2-Bis[4,5-dihydro-3H-binaptho(1,2-c:2',1'-e)phosphepino]benzene
BIPHEMP (6,6'-Dimethylbiphenyl-2,2'-diyl)bis(diphenyl-phosphine)
BOC tert-butoxycarbonyl
(Boc)$_2$O Di-tert-butyl dicarbonate
CBS Corey-Bakshi-Shibata catalyst
CBZ benzyloxycarbonyl, carbobenzyloxy
COD 1,5-cyclooctadiene
CPME cyclopentyl methyl ether
de diastereomeric excess
DIPEA diisopropylethylamine
DMAP dimethylamino pyridine
DMF N,N-dimethylformamide
DPEN 1,2-Diphenyl ethylenediamine
ee enantiomeric excess
Et ethyl
EtOAc ethyl acetate
Fmoc 9-Fluorenylmethyloxycarbonyl
(2-Furyl)-MeOBIPHEP (6,6'-Dimethoxybiphenyl-2,2'-diyl)bis[bis(2-furyl)-phosphine]
HAP hazardous air pollutant
HBTU N,N,N',N'-Tetramethyl-O-(1H-benzotriazol-1-yl) uronium hexafluorophosphate
iBu iso-butyl
ICM International Conference on Harmonisation
IPC in process control
iPr iso-propyl
iPr-DUPHOS 1,2-Bis(2,5-di-i-propylphospholano)benzene
Me methyl
MeOBIPHEP (6,6'-Dimethoxybiphenyl-2,2'-diyl)bis(diphenyl-phosphine)
MES 2-(N-morpholino)ethanesulfonic acid
MTBE methyl tert-butyl ether
NAD Nicotinamide adenine dinucleotide
NADP Nicotinamide adenine dinucleotide phosphate
nBu n-butyl
NEM N-ethyl morpholine
nPr n-propyl
OAc acetate
PBS potassium dihydrogen phosphate buffer
pCym p-cymene
PDE permitted daily exposure
Ph phenyl
pTol p-tolyl
pTol-Binap 2,2'-Bis(di-p-tolylphosphino)-1,1'-binaphthyl
S/C substrate-to-catalyst molar ratio
T3P Propylphosphonic anhydride
tBu tert-butyl
t-BuOK potassium tert-butoxid
TEA triethylamine
TFA trifluoro acetate
THF tetrahydrofuran TMBTP 2,2',5,5'-Tetramethyl-4,4'-bis(diphenylphosphino)-3,3'-bithiophene
TPA tri(n-propyl)amine
Xyl 3,5-dimethylphenyl
3,5-Xyl,4-MeO-MeOBIPHEP (6,6'-Dimethoxybiphenyl-2,2'-diyl)bis[bis(3,5-dimethyl-4-methoxy-phenyl)¬phosphine]
3,5-Xyl-BINAP 2,2'-Bis[di(3,5-xylyl)phosphine]-1,1'-binaphthyl
3,5-Xyl-MeOBIPHEP (6,6'-Dimethoxybiphenyl-2,2'-diyl)bis[bis(3,5-dimethylphenyl)¬phosphine]

The present invention provides a processes for the preparation of a compound of formula (I) or salts thereof, which comprise the coupling reaction of a compound of formula (II) with a compound of formula (III), wherein $R^1$, $R^2$ and M are as described herein (Scheme 1 below).

One further aspect of present invention relates to the process for the manufacture of compounds of formula (II) comprising the asymmetric hydrogenation of a compound of formula (IV) using a metal complex catalyst (C) (Scheme 1 below).

One aspect of present invention relates to the process for the manufacture of compounds of formula (III) comprising the asymmetric reduction of compound of formula (V) catalyzed by an oxidoreductase (Scheme 1 below).

One further aspect of present invention relates to the process for the manufacture of compounds of formula (VI) or pharmaceutically acceptable salts thereof, wherein a compound of formula (I) is deprotected (Scheme 1 below).

Scheme 1

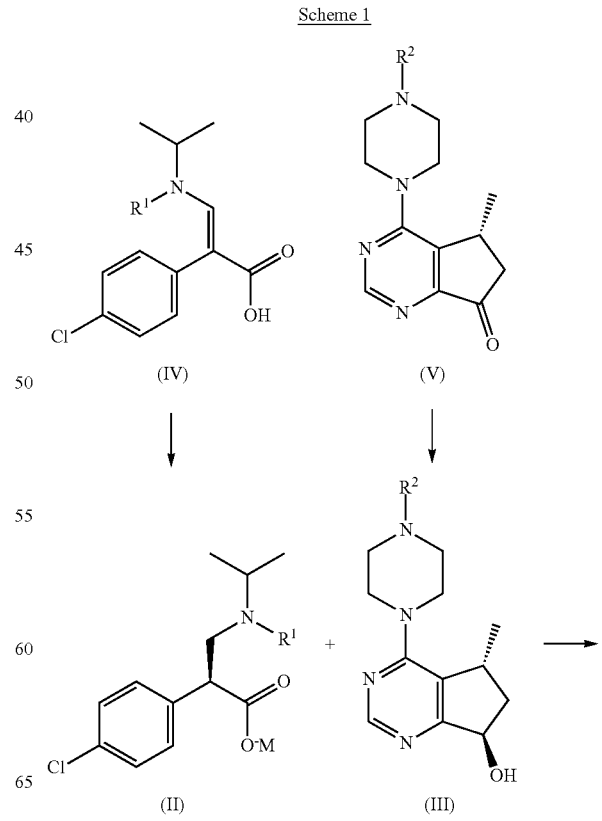

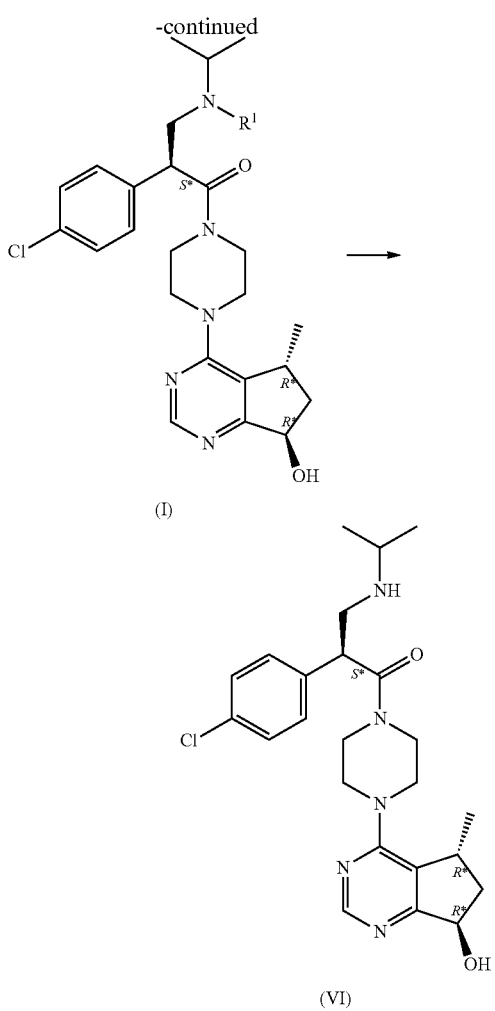

(I)

(VI)

In one embodiment of the invention, $R^1$ is an amino-protecting group selected from the list of benzyl, benzyloxycarbonyl (carbobenzyloxy, CBZ), 9-Fluorenylmethyloxycarbonyl (Fmoc), p-methoxybenzyloxycarbonyl, p-nitrobenzyloxycarbonyl, tert-butoxycarbonyl (BOC), and trifluoroacetyl.

In a particular embodiment of the invention, $R^1$ is tert-butoxycarbonyl (BOC).

In one embodiment of the invention, $R^2$ is an amino-protecting group selected from the list of benzyl, benzyloxycarbonyl (carbobenzyloxy, CBZ), 9-Fluorenylmethyloxycarbonyl (Fmoc), p-methoxybenzyloxycarbonyl, p-nitrobenzyloxycarbonyl, tert-butoxycarbonyl (BOC), and trifluoroacetyl.

In a particular embodiment of the invention, $R^2$ is tert-butoxycarbonyl (BOC).

In one embodiment of the invention, M is a metal ion selected from the list of alkali metal ion, alkaline earth metal ion and transition metal ion.

In a particular embodiment of the invention, M is a metal ion, particularly an alkali metal ion, alkaline earth metal ion or transition metal ion with the proviso that it is not $K^+$.

In a particular embodiment of the invention, M is an alkali metal ion.

In a particular embodiment of the invention, M is $Li^+$, $K^+$ or $Na^+$.

In a particular embodiment of the invention, M is not $K^+$.

In the most particular embodiment of the invention, M is $Na^+$.

WO 2008/006040 discloses amino acids of formula (II-pa) and methods of manufacture thereof, wherein $R^6$ and $R^9$ can have various alternatives and t is 0 to 4.

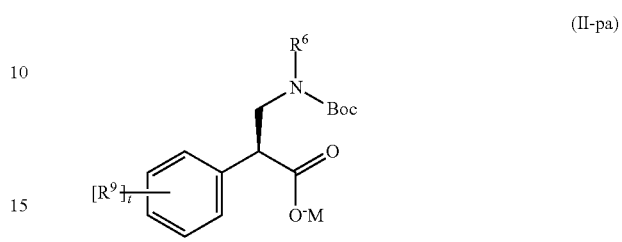

(II-pa)

Therein disclosed processes for the manufacture of compounds of formula (II-pa) either involve a) the non-enantioselective reaction of an alkylamine with 2-arylacrylate to yield a racemic mixture or b) the asymmetric addition of an alkoxymethanamine to 2-phenylacetate containing an appropriate chiral auxiliary. Both processes do not involve an asymmetric hydrogenation but an addition reaction. Consequently, both processes require additional steps for addition, cleavage and separation of the auxiliary.

The synthesis according to method a) above proceeds via the formation of a racemic ester intermediate which is further hydrolyzed to the racemic acid, coupled with a chiral auxiliary (as only e.g. S enantiomer) to generate a 50:50 mixture of diastereomers R-aminoacid/S-auxiliary and S-aminoacid/S-auxiliary. The diastereomers have to be separated by chromatography. The yield of the desired S—S intermediate is only 38%. Additionally, the S—S intermediate has to be hydrolyzed to afford the S-II acid (with loss of the other chiral component, the chiral auxiliary). This procedure is lengthy and poorly efficient since in one step 72% of the material is lost. In summary, the non-enantioselective addition of amine and acrylate exhibits the intrinsic problem of lack of stereoselectivity and thus mandatory separation of the racemic mixture by e.g. chromatography. Consequently, the yield is at least 100% lower as compared to a stereoselective sequence.

Also the asymmetric addition to an intermediate containing a chiral auxiliary (method b) above) requires additional steps for addition, cleavage and separation of the auxiliary. A precursor in the synthesis of the targeted acid is combined with a chiral auxiliary and the resulting intermediate is coupled with an alkoxymethanamine. The product consists then at best of a slightly enriched mixture of diastereoisomers R/S and S/S, if not of a 1:1 mixture, which have to be treated further as mentioned above to isolate the (S)-isomer of the compound of formula (II-pa) in at best modest yield.

There is thus an unmet need for improved processes for the preparation of compounds of formula (II) which provide a better stereoselectivity making subsequent chiral chromatography void, which require less reaction steps, which provide a higher yield and which are therefore more efficient, greener and less costly.

Inventors of present invention have found a new process for the manufacture of compounds of formula (II) which comprises the asymmetric hydrogenation of a compound of formula (IV) using a metal complex catalyst (C).

This new process for the manufacture of compounds of formula (II) features a number of relevant benefits as compared to processes known in the art:

A highly stereoselective reaction is introduced in the synthesis;
Subsequent purification using chiral chromatography is void;
The number of reaction steps is decreased;
Overall yield is improved;
Overall reaction is more efficient, greener and less costly.

The particular metal complex catalysts of present invention have been found to be much more efficient and much more active and selective than other known catalysts in the sense that under similar reaction conditions (i.e. without additives) a substrate-to-catalyst molar ratio (S/C) of up to 10'000 can be employed whereas other known catalysts need to be used at a S/C of 200-250. Thus, the use of 40-50 times less catalyst has a substantial impact on efficiency, costs and greenness.

Certain known catalysts require a large quantity of $LiBF_4$ as additive (up to 5.8 mol % towards the hydrogenation substrate, up to 100 molar equivalents towards the catalyst) to increase the catalysts activity. High amounts of $LiBF_4$ are disadvantageous for an industrial process, because the presence of this large amount of fluoride ions (up to 23.2% of the hydrogenation substrate) poses a problem as to the corrosion of the steel pressure reactors on scale-up. On the other hand, even with $LiBF_4$ additive the catalyst does not reach the activity of our new catalysts (e.g. up to S/C 10'000).

Homogeneously catalyzed reactions such e.g. asymmetric hydrogenations as known in the art require very laborious work-up procedures, comprising many cycles of extractions and concentration of solutions. Further, asymmetric hydrogenations as known in the art require the removal of metal catalysts with a scavenger (e.g. thiol resins) in large amounts (up to 6% wt towards hydrogenation substrate; up to 193 times the weight of the catalyst). Such removal of ruthenium contaminants using scavenger resins is by far not easy and quite expensive. In addition, the ruthenium content is reduced only in part (e.g. to about 50 ppm) and is carried through into next step, so increasing the potential for by-products formation. This adds material and labor costs and opens the discussion about potential impurities.

In conclusion, the efficiency of known purification and isolation processes of the hydrogenation product from the catalysts and additives is low.

In contrast, the process according to the invention provides salts of the compound of formula (II) which are precipitated directly from the hydrogenation mixture and which can easily be filtered off. Such isolation and purification of the hydrogenation product provides high yields (>94%) with 100% ee and with ruthenium content below the detection limit of 5 ppm. The work-up of the reaction product of the asymmetric hydrogenation as found by present inventors is thus substantially simpler, cheaper and more useful than conventional processes.

One aspect of present invention relates to a compound of formula (II)

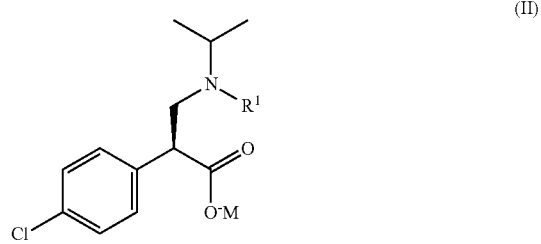

(II)

wherein $R^1$ and M are as defined herein.

One aspect of present invention relates to a compound of formula (II) which is sodium (S)-3-(tert-butoxycarbonyl (isopropyl)amino)-2-(4-chlorophenyl)propanoate.

One aspect of present invention relates to the process for the manufacture of compounds of formula (II)

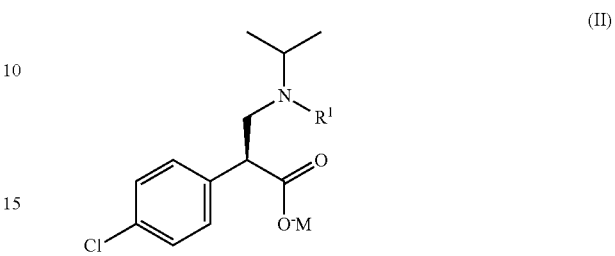

(II)

comprising the asymmetric hydrogenation of a compound of formula (IV)

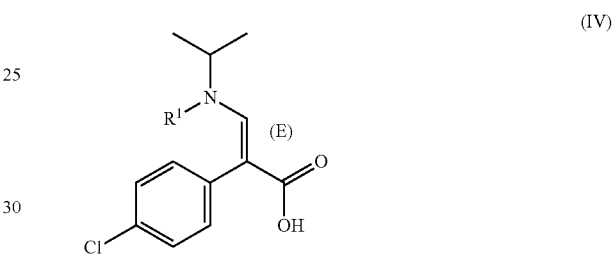

(IV)

using a metal complex catalyst (C) wherein $R^1$ and M are as defined herein.

In one embodiment of the invention, the metal complex catalyst (C) is a ruthenium complex catalyst.

In one embodiment of the invention, the ruthenium complex catalyst comprises ruthenium characterized by the oxidation number II.

In one embodiment of the invention, the ruthenium complex catalyst comprises a chiral phosphine ligand (D).

In one embodiment of the invention, the ruthenium complex catalyst comprises ligands, particularly neutral ligands (L) and/or anionic ligands (Z).

Examples of neutral ligands (L) are olefins such as ethylene or propylene, cyclooctene, 1,3-hexadiene, norbornadiene, 1,5-cyclooctadiene, benzene, hexamethylbenzene, 1,3,5-trimethylbenzene, and p-cymene or also solvents such as tetrahydrofuran, dimethylformamide, acetonitrile, benzonitrile, acetone, toluene and methanol.

Examples of anionic ligands (Z) are acetate ($CH_3COO^-$), trifluoroacetate ($CF_3COO^-$), $\eta^5$-2,4-pentadienyl, $\eta^5$-2,4-dimethyl-pentadienyl, and halogen ions such as fluoride, chloride, bromide, or iodide.

If the ruthenium complex catalyst is charged, it further comprises non-coordinating anions (Y). Examples of non-coordinating anions (Y) are halogen ions such as fluoride, chloride, bromide, or iodide, $BF_4^-$, $ClO_4^-$, $SbF_6^-$, $PF_6^-$, $B(phenyl)_4^-$, $B(3,5-di-trifluoromethyl-phenyl)_4^-$, $CF_3SO_3^-$, and $C_6H_5SO_3^-$.

The ruthenium complex catalyst can optionally further be coordinated to a Lewis acid, such as $AlCl_3$.

In one embodiment of the invention, the ruthenium complex catalyst is selected from a compound of formula (C1), (C2) or (C3):

Ru(Z)₂D   (C1)

[Ru(Z)$_{2-p}$(D)(L)$_m$](Y)$_p$   (C2)

Ru(E)(E')(D)(F)   (C3)

wherein:
D is a chiral phosphine ligand;
L is a neutral ligand selected from $C_{2-7}$ alkene, cyclooctene, 1,3-hexadiene, norbornadiene, 1,5-cyclooctadiene, benzene, hexamethylbenzene, 1,3,5-trimethylbenzene, p-cymene, tetrahydrofuran, dimethylformamide, acetonitrile, benzonitrile, acetone, toluene and methanol;
Z is an anionic ligand selected from hydride, fluoride, chloride, bromide, $\eta^5$-2,4-pentadienyl, $\eta^5$-2,4-dimethyl-pentadienyl or the group A-COO⁻, with the proviso that when two Z are attached to the Ru atom they can either be the same or different;
A is $C_{1-7}$ alkyl, $C_{1-7}$ haloalkyl, aryl, or haloaryl;
Y is a non-coordinating anion selected from fluoride, chloride, bromide, $BF_4^-$, $ClO_4^-$, $SbF_6^-$, $PF_6^-$, B(phenyl)$_4^-$, B(3,5-di-trifluoromethyl-phenyl)$_4^-$, $CF_3SO_3^-$, and $C_6H_5SO_3^-$;
F is an optionally chiral diamine;
E and E' are both halogen ions, or E is hydride and E' is $BH_4^-$;
m is 1, 2, 3 or 4;
p is 1 or 2.

In a particular embodiment of the invention, the ruthenium complex catalyst is selected from a compound of formula (C1) or (C2) wherein Z, D, L, Y, m and p are as described herein.

In a particular embodiment of the invention, the ruthenium complex catalyst is selected from a compound of formula (C1), wherein Z and D are as described herein.

In a particular embodiment of the invention, the ruthenium complex catalysts is Ru(Z)₂D, wherein Z and D are as described herein.

In a particular embodiment of the invention, the ruthenium complex catalyst is selected from a compound of formula (C2), wherein Z, D, L, Y, m and p are as described herein.

In a particular embodiment of the invention, the ruthenium complex catalyst is selected from a compound of formula (C3), wherein E, E', D and F are as described herein.

In a particular embodiment of the invention, the anionic ligand (Z) is independently selected from chloride, bromide, iodide, OAc, and TFA.

In a particular embodiment of the invention, the anionic ligand (Z) is A-COO⁻.

In a particular embodiment of the invention, A is —$CF_3$.

In a particular embodiment of the invention, the anionic ligand (Z) is trifluoroacetate (TFA).

In a particular embodiment of the invention, the neutral ligand (L) is independently selected from benzene ($C_6H_6$), p-cymene (pCym), and acetonitrile (AN).

In a particular embodiment of the invention, the neutral ligand (L) is benzene ($C_6H_6$).

In a particular embodiment of the invention, the non-coordinating anion (Y) is selected from chloride, bromide, iodide and $BF_4^-$.

In a particular embodiment of the invention, the non-coordinating anion (Y) is $BF_4^-$.

In a particular embodiment of the invention, m is 1 or 4.
In a particular embodiment of the invention, m is 1.
In a particular embodiment of the invention, m is 4.

In a particular embodiment of the invention, p is 1.
In a particular embodiment of the invention, p is 2.
In a particular embodiment of the invention, E and E' are both chloride;
In a particular embodiment of the invention, the chiral diamine F is (1S,2S)-1,2-diphenylethylenediamine (S,S-DPEN).

In a particular embodiment of the invention, the ruthenium complex catalyst is coordinated to a Lewis acid, particularly $AlCl_3$.

In one embodiment of the invention, the chiral phosphine ligand D is selected from a compound of formula (D1) to (D12):

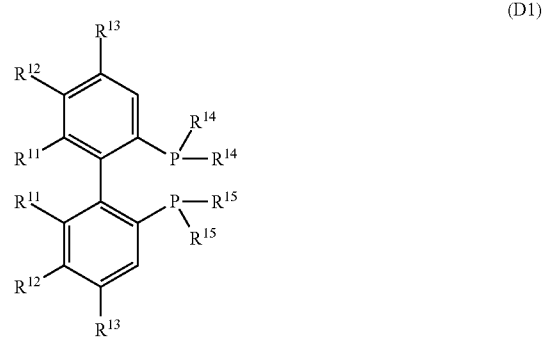

(D1)

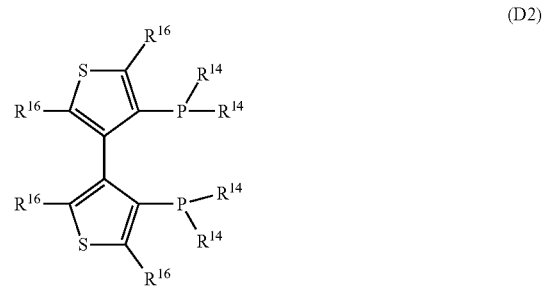

(D2)

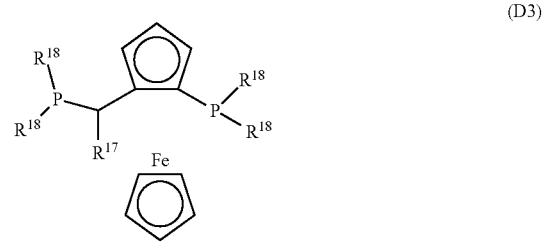

(D3)

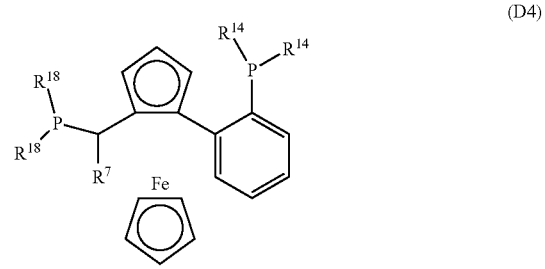

(D4)

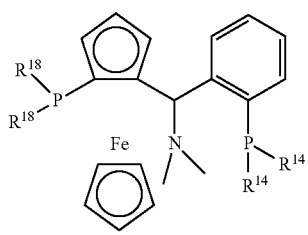
(D5)

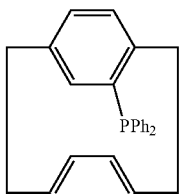
(D11)

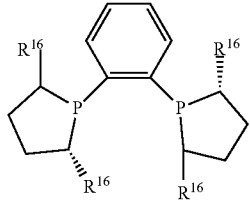
(D6)

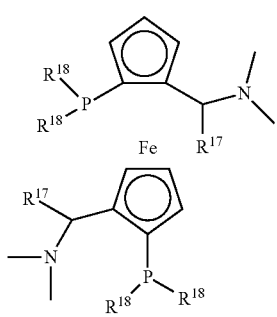
(D7)

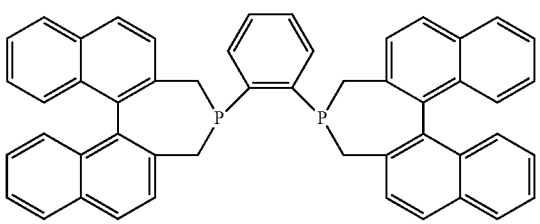
(D12)

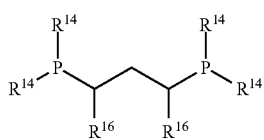
(D8)

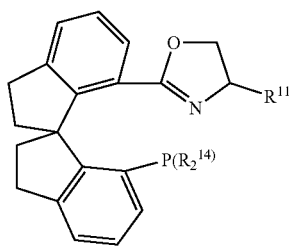
(D9)

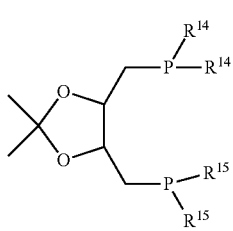
(D10)

wherein:
$R^{11}$ is $C_{1-7}$ alkyl, $C_{1-7}$ alkoxy, benzyloxy, hydroxy or $C_{1-7}$ alkyl-C(O)O—;

$R^{12}$ and $R^{13}$ are each independently hydrogen, $C_{1-7}$ alkyl, $C_{1-7}$ alkoxy or di($C_{1-7}$ alkyl)amino; or $R^{11}$ and $R^{12}$ which are attached to the same phenyl group, or $R^{12}$ and $R^{13}$ which are attached to the same phenyl group taken together are —X—(CH$_2$)$_r$—Y—, wherein X is —O—, or —C(O)O—, Y is —O—, —N(lower-alkyl)-, or —CF$_2$— and r is an integer from 1 to 6; or two $R^{11}$ taken together are —O—(CH$_2$), —O— or O—CH(CH$_3$)—(CH$_2$)$_5$—CH(CH$_3$)—O—, wherein s is an integer from 1 to 6; or $R^{11}$ and $R^{12}$, or $R^{12}$ and $R^{13}$, together with the carbon atoms to which they are attached, form a naphthyl, tetrahydronaphthyl or dibenzofuran ring;

$R^{14}$ and $R^{15}$ are each independently $C_{1-7}$ alkyl, $C_{3-8}$ cycloalkyl, phenyl, naphthyl or heteroaryl, optionally substituted with 1 to 7 substituents independently selected from the group consisting of $C_{1-7}$ alkyl, $C_{1-7}$ alkoxy, di($C_{1-7}$ alkyl)amino, morpholinyl, phenyl, tri($C_{1-7}$ alkyl)silyl, $C_{1-7}$ alkoxycarbonyl, hydroxycarbonyl, hydroxysulfonyl, (CH$_2$)$_t$—OH and (CH$_2$)$_t$—NH$_2$, wherein t is an integer from 1 to 6;

$R^{16}$ is $C_{1-7}$ alkyl;

$R^{17}$ is $C_{1-7}$ alkyl; and $R^{18}$ independently is aryl, heteroaryl, $C_{3-8}$ cycloalkyl or $C_{1-7}$ alkyl.

In a particular embodiment of the invention, the chiral phosphine ligand (D) is selected from the compound of formula (D1), wherein $R^{11}$ to $R^{15}$ are as described herein.

In a particular embodiment of the invention, the chiral phosphine ligand (D) is selected from (R)-3,5-Xyl-BINAP, (R)-BINAP, (S)-2-Furyl-MeOBIPHEP, (S)-BINAP, (5)-BINAPHANE, (S)-BIPHEMP, (S)-MeOBIPHEP, (S)-pTol-BINAP), (S)-TMBTP and (S,S)-iPr-DUPHOS.

In a particular embodiment of the invention, the chiral phosphine ligand (D) is selected from (S)-BIPHEMP, (S)-BINAP, and (S)-MeOBIPHEP.

In a particular embodiment of the invention, the chiral phosphine ligand (D) is (S)-BINAP.

In a particular embodiment of the invention, the chiral phosphine ligand (D) is (S)-2,2'-Bis(diphenylphosphino)-1,1'-binaphthyl.

In a particular embodiment of the invention, the chiral phosphine ligand (D) is

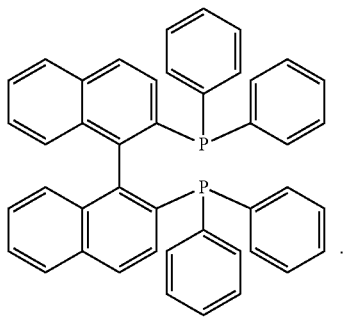 [SMILES: c1ccc(P(c2ccccc2)c2ccc3ccccc3c2-c2c(P(c3ccccc3)c3ccccc3)ccc3ccccc23)cc1]

In a particular embodiment of the invention, the ruthenium complex catalyst is selected from the group of:
Ru(TFA)$_2$((R)-3,5-Xyl-BINAP),
Ru(OAc)$_2$((S)-2-Furyl-MeOBIPHEP),
Ru(OAc)$_2$((S)-BINAP),
[Ru(OAc)$_2$((S)-BINAP)]AlCl$_3$,
Ru(TFA)$_2$((S)-BINAP),
Ru(TFA)$_2$((S)-BINAPHANE),
Ru(TFA)$_2$((S)-BIPHEMP),
Ru(OAc)$_2$((S)-MeOBIPHEP),
Ru(TFA)$_2$((S)-TMBTP),
Ru(TFA)$_2$((S,S)-iPr-DUPHOS),
[Ru((R)-BINAP)(pCym)(AN)](BF$_4$)$_2$,
[RuBr((S)-BINAP)(C$_6$H$_6$)]Br,
[RuCl((S)-BINAP)(C$_6$H$_6$)]BF$_4$,
[RuCl((S)-BINAP)(C$_6$H$_6$)]Cl,
[RuI((S)-BINAP)(C$_6$H$_6$)]I,
[Ru((S)-BINAP)(AN))$_4$](BF$_4$)$_2$, and
RuCl$_2$((S)-pTol-BINAP)(S, S-DPEN).

In a particular embodiment of the invention, the ruthenium complex catalyst is selected from the group of:
Ru(TFA)$_2$((R)-3,5-Xyl-BINAP),
Ru(OAc)$_2$((S)-2-Furyl-MeOBIPHEP),
Ru(OAc)$_2$((S)-BINAP),
[Ru(OAc)$_2$((S)-BINAP)]AlCl$_3$,
Ru(TFA)$_2$((S)-BINAP),
Ru(TFA)$_2$((S)-BINAPHANE),
Ru(TFA)$_2$((S)-BIPHEMP),
Ru(OAc)$_2$((S)-MeOBIPHEP),
Ru(TFA)$_2$((S)-TMBTP),
Ru(TFA)$_2$((S,S)-iPr-DUPHOS),
[Ru((R)-BINAP)(pCym)(AN)](BF$_4$)$_2$,
[RuBr((S)-BINAP)(C$_6$H$_6$)]Br,
[RuCl((S)-BINAP)(C$_6$H$_6$)]BF$_4$,
[RuI((S)-BINAP)(C$_6$H$_6$)]I,
[Ru((S)-BINAP)(AN))$_4$](BF$_4$)$_2$, and
RuCl$_2$((S)-pTol-BINAP)(S,S-DPEN).

In a particular embodiment of the invention, the ruthenium complex catalyst is a compound of formula (C1) selected from the group of:
Ru(TFA)$_2$((R)-3,5-Xyl-BINAP),
Ru(OAc)$_2$((S)-2-Furyl-MeOBIPHEP),
Ru(OAc)$_2$((S)-BINAP),
[Ru(OAc)$_2$((S)-BINAP)]AlCl$_3$,
Ru(TFA)$_2$((S)-BINAP),
Ru(TFA)$_2$((S)-BINAPHANE),
Ru(TFA)$_2$((S)-BIPHEMP),
Ru(OAc)$_2$((S)-MeOBIPHEP),
Ru(TFA)$_2$((S)-TMBTP), and
Ru(TFA)$_2$((S,S)-iPr-DUPHOS).

In a particular embodiment of the invention, the ruthenium complex catalyst is a compound of formula (C2) selected from the group of:
[Ru((R)-BINAP)(pCym)(AN)](BF$_4$)$_2$,
[RuBr((S)-BINAP)(C$_6$H$_6$)]Br,
[RuCl((S)-BINAP)(C$_6$H$_6$)]BF$_4$,
[RuCl((S)-BINAP)(C$_6$H$_6$)]Cl,
[RuI((S)-BINAP)(C$_6$H$_6$)]I, and
[Ru((S)-BINAP)(AN)$_4$](BF$_4$)$_2$.

In a particular embodiment of the invention, the ruthenium complex catalyst is a compound of formula (C3), particularly RuCl$_2$((S)-pTol-BINAP)(S,S-DPEN)).

In a particular embodiment of the invention, the ruthenium complex catalyst is Ru(TFA)$_2$((S)-BINAP).

In a particular embodiment of the invention, the ruthenium complex catalyst is [RuCl(S-BINAP)(C$_6$H$_6$)]C$_1$.

In a particular embodiment of the invention, the ruthenium complex catalyst is not [RuCl(S-BINAP)(C$_6$H$_6$)]C$_1$.

In a particular embodiment of the invention, the asymmetric hydrogenation of a compound of formula (IV) is carried out in a solvent selected from alcohols, hydrocarbons, chlorinated hydrocarbons, fluorinated and polyfluorinated aliphatic or aromatic hydrocarbons, supercritical or liquid carbon dioxide, THF, water or mixtures thereof.

Particular solvents for the asymmetric hydrogenation are alcohols, chlorinated hydrocarbons and THF.

Particular solvents for the asymmetric hydrogenation are selected from the list of MeOH, EtOH, i-PrOH, EtOH/cyclopentyl methyl ether, EtOH/CH$_2$Cl$_2$, EtOH/EtOAc, EtOH/THF, EtOH/H$_2$O, CH$_2$Cl$_2$ and THF.

Most particular solvent for the asymmetric hydrogenation is ethanol (EtOH).

The solvents can be used alone or as mixture of solvents mentioned above.

In a particular embodiment of the invention, the asymmetric hydrogenation of a compound of formula (IV) is carried out at a concentration of the compound of formula (IV) of 1 to 50% wt, particularly 5% wt, 10% wt, 20% wt or 30% wt.

In a particular embodiment of the invention, the asymmetric hydrogenation of a compound of formula (IV) is carried out a concentration of 10 to 25% wt of the compound of formula (IV).

It has surprisingly been found that in special cases, the addition of certain additives improves the asymmetric hydrogenation of a compound of formula (IV). It is hypothesized that the activity as well as the stability of the Ruthenium catalyst is substantially improved and therefore the amount of catalyst required is reduced. Lower amounts of catalyst employed results in simplified work-up and reduced costs.

In a particular embodiment of the invention, the asymmetric hydrogenation of a compound of formula (IV) further comprises one or more additives selected from the list of LiBF$_4$, LiPF$_6$, LiO$_3$SCF$_3$, NaCl, NaBr, NaI, KCl, KBr, KI, LiCl, LiBr, LiI, HBF$_4$, HCl, HBr, H$_2$SO$_4$, and CH$_3$SO$_3$H.

In a particular embodiment of the invention, the asymmetric hydrogenation of a compound of formula (IV) does not comprise LiBF$_4$, LiPF$_6$ or LiO$_3$SCF$_3$ as additive. In view of their highly corrosive character, such fluoride containing additives are difficult to handle and are thus not preferred.

In a particular embodiment of the invention, the asymmetric hydrogenation of a compound of formula (IV) further comprises one or more additives selected from the list of NaCl, NaBr, KCl, KBr, HCl and HBr.

In a particular embodiment of the invention, the asymmetric hydrogenation of a compound of formula (IV) further comprises one or more additives selected from the list of LiBF$_4$, HBF$_4$, HCl, H$_2$SO$_4$, and CH$_3$SO$_3$H.

In a particular embodiment of the invention, the asymmetric hydrogenation of a compound of formula (IV) further comprises one or more additives selected from the list of LiBF$_4$, NaCl, NaBr, LiCl, LiBr, LiI, HBF$_4$, HCl, HBr, H$_2$SO$_4$, and CH$_3$SO$_3$H.

In a particular embodiment of the invention, the asymmetric hydrogenation of a compound of formula (IV) is carried out with hydrogen as hydrogen source.

In a particular embodiment of the invention, the asymmetric hydrogenation of a compound of formula (IV) is carried out under hydrogen pressure of 1 to 150 bar, particularly 10 to 30 bar, most particularly 17 to 21 bar.

In a particular embodiment of the invention, the asymmetric hydrogenation of a compound of formula (IV) is carried out a temperature of 10 to 120° C., particularly 20 to 90° C.

In a particular embodiment of the invention, the asymmetric hydrogenation of a compound of formula (IV) is carried out during a time period of 5 to 30 h, particularly 6 to 25 h, more particularly 6 to 23 h.

In a particular embodiment of the invention, the asymmetric hydrogenation of a compound of formula (IV) is carried out at a substrate/catalyst ratio (S/C) of 5 to 100'000, particularly 100 to 15'000, most particularly 100 to 10'000.

In a particular embodiment of the invention, the asymmetric hydrogenation of a compound of formula (IV) is carried out batchwise.

In a particular embodiment of the invention, the asymmetric hydrogenation of a compound of formula (IV) is carried out in a continuous manner.

One aspect of present invention relates to the process for the manufacture of compounds of formula (II)

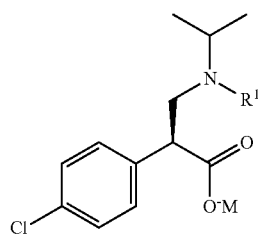

(II)

comprising the asymmetric hydrogenation of a compound of formula (IV)

(IV)

using a metal complex catalyst (C), followed by forming a salt by adding to the hydrogenation reaction mixture an alcoholic solution of a metal alkoxide of formula C$_{1-7}$ alkyl-OM, wherein R$^1$ and M are as defined herein.

One aspect of present invention relates to the process for the manufacture of compounds of formula (II) comprising the asymmetric hydrogenation of a compound of formula (IV) using a metal complex catalyst (C), followed by forming a salt by adding to the hydrogenation reaction mixture an alcoholic solution of a metal alkoxide of formula C$_{1-7}$ alkyl-OM, without prior isolation or purification of the acid intermediate, wherein R$^1$ and M are as defined herein.

In a particular embodiment of the invention, the metal alkoxide employed in the salt forming step is MeOM, EtOM, iPrOM, nPrOM, nBuOM, iBuOM or tBuOM, most particularly EtOM.

In a particular embodiment of the invention, the alcohol used as solvent in the salt forming step is C$_{1-7}$ alkyl-OH, more particularly MeOH, EtOH, iPrOH, nPrOH, nBuOH, iBuOH or tBuOH, most particularly EtOH.

One aspect of present invention relates to the process for the manufacture of compounds of formula (II) comprising the asymmetric hydrogenation of a compound of formula (IV) using a metal complex catalyst (C), followed by forming a salt by adding to the hydrogenation reaction mixture an ethanolic solution of sodium ethoxide.

Compounds of formula (IV) can be prepared according to methods known to those skilled in the art. A particular general method of preparation of compounds of formula (IV) is depicted in Scheme 2. For a more detailed description of the individual reaction steps, see the Examples section below.

Scheme 2

(IVa)

(IVb)

(IVc)

A compound of formula (IVa), wherein R$^3$ is optionally substituted C$_{1-7}$ alkyl, particularly ethyl, is condensed under basic conditions with a compound HCO$_2$R$^4$, wherein R$^4$ is optionally substituted C$_{1-7}$ alkyl, particularly ethyl, to form a compound of formula (IVb). Further condensation of compounds of formula (IVb) with an amine HN(isopropyl)

$R^5$, wherein $R^5$ is hydrogen, $C_{1-7}$ alkyl or an amino protecting group, forms compounds of formula (IVc). When $R^5$ is hydrogen in compounds of formula (IVc), additional protection of the amine can be done to form protected compounds of formula (IVc) (e.g., where $R^5$ is an amino protecting group, such as Boc). Hydrolysis of the ester of compound (IVc) provides compounds of formula (IV).

The ruthenium complex catalysts of the invention can in principle be prepared in a manner known per se. They can be isolated or used directly (in situ preparation) e.g. according to B. Heiser et al., *Tetrahedron: Asymmetry* 1991, 2, 51; or N. Feiken et al., *Organometallics* 1997, 16, 537; or J.-P. Genet, *Acc. Chem. Res.* 2003, 36, 908; or K. Mashima et al., *J. Org. Chem.* 1994, 53, 3064; *Angew. Chem. Int. Ed.* 1998, 37, 1703-1707; or M. P. Fleming et al., U.S. Pat. No. 6,545,165 B1, and references cited therein; as well as O. Briel et al. in *Catalysis of Organic Reactions*, CRC Press, Boca Raton, 2009 specifically for ferrocene-based Ru-complexes, the disclosures of all these documents are incorporated herein by reference in their entirety for all purposes.

The synthesis of [Ru(TFA)$_2$((S)-BINAP)] is disclosed in B. Heiser et al, *Tetrahedron: Asymmetry* 1991, 2, 51.

The ruthenium complex catalysts can be prepared in situ, i.e. just before use and without isolation. The solution in which such a catalyst is prepared can already contain the substrate for the enantioselective hydrogenation or the solution can be mixed with the substrate just before the hydrogenation reaction is initiated.

WO 2008/006040 discloses 5-methyl-6,7-dihydro-5H-cyclopenta[d]pyrimidin-7-ols of formula (71) and methods of manufacture thereof, wherein $R^5$ can have various alternatives.

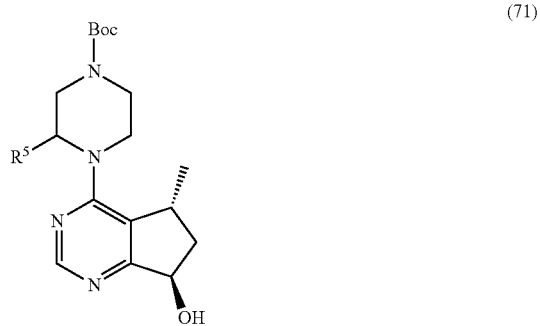

(71)

In particular, WO 2008/006040 discloses the asymmetric reduction of 5-methyl-5,6-dihydrocyclopenta[d]pyrimidin-7-ones to (R) or (S)-5-methyl-6,7-dihydro-5H-cyclopenta[d]pyrimidin-7-ols using a chiral catalyst in the presence of hydrogen, a Corey-Bakshi-Shibata (CBS) catalyst, a borohydride reducing agent in the presence of a chiral ligand, or a non-chiral reducing agent (e.g. H$_2$, Pd/C).

The methods known in the art to produce compounds of formula (III) exhibit the intrinsic drawbacks that they require drastic reaction conditions (e.g. high pressures), the use of heavy metals and chiral auxiliaries, and the obtained diastereoselectivity is only limited (i.e. 88% de) thus requiring additional purification steps.

Inventors of present invention have found new enzymatic processes for the manufacture of compounds of formula (III), wherein $R^2$ is as described herein.

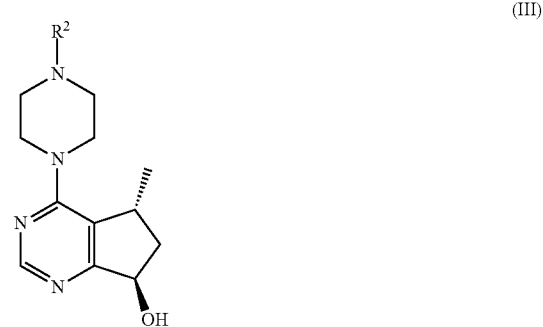

(III)

These new processes for the manufacture of compounds of formula (III) according to present invention feature a number of relevant benefits as compared to the process as known in the art. The advantages of the enzymatic reduction are its catalytic nature, the very high diastereoselectivity avoiding the potential need of a subsequent resolution of the diastereomers formed and the mild reaction conditions. In addition, no heavy metals and chiral auxiliaries are required.

The enzymatic reduction of the present invention simplifies the technical requirements, reduces the number and amounts of ingredients and enables a higher space-time-yield. The advantages of the present invention are exemplified as the improved technical relevant criteria such as increased substrate concentration (up to 25%), increased product concentration (up to 25%), decreased cofactor loading (down to ⅓000 of the compound of formula (V)) and a simpler cofactor regeneration system with a 2-propanol as final reductant. The cofactor regeneration system with 2-propanol as final reductant avoids a second enzyme, reduces the viscosity, avoids the continuous neutralization of the gluconic acid as the oxidized cosubstrate and allows the continuous removal of the acetone formed.

One aspect of present invention relates to the process for the manufacture of compounds of formula (III)

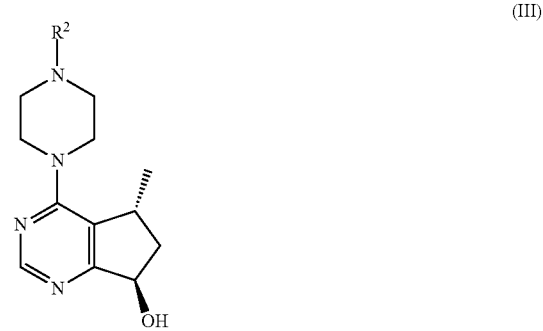

(III)

comprising the asymmetric reduction of the compound of formula (V)

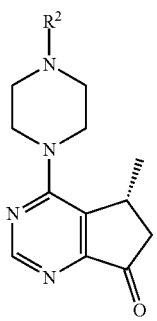

catalyzed by an oxidoreductase, wherein $R^2$ is as defined herein.

In one aspect of the invention, the oxidoreductase catalyzing the asymmetric reduction of a compound of formula (V) to a compound of formula (III) is a ketoreductase.

In one aspect of the invention, the oxidoreductase catalyzes the asymmetric reduction of a compound of formula (V) to a compound of formula (III) with a diastereoselectivity of at least 95% diastereomeric excess (de), particularly with a diastereoselectivity of at least 98% de, more particularly with a diastereoselectivity of at least 99% de.

In one aspect of the invention, the asymmetric reduction of a compound of formula (V) to a compound of formula (III) is catalyzed by an oxidoreductase in the presence of a cofactor.

In one aspect of the invention, the cofactor which is oxidized in the asymmetric reduction of a compound of formula (V) to a compound of formula (III) is NADH or NADPH.

In one aspect of the invention, the cofactor which is oxidized in the asymmetric reduction of a compound of formula (V) to a compound of formula (III) is in situ regenerated applying either the enzyme-coupled cofactor regeneration (e.g. based on glucose as final reductant and glucose dehydrogenase) or the substrate coupled regeneration (e.g. using a secondary alcohol as cosubstrate).

In one aspect of the invention, the cofactor which is oxidized in the asymmetric reduction of a compound of formula (V) to a compound of formula (III) is in situ regenerated by enzyme-coupled cofactor regeneration using glucose and glucose dehydrogenase as cosubstrate.

In one aspect of the invention, the cofactor which is oxidized in the asymmetric reduction of a compound of formula (V) to a compound of formula (III) is in situ regenerated by substrate-coupled regeneration using a secondary alcohol as cosubstrate.

In one aspect of the invention, the secondary alcohol as cosubstrate for the substrate coupled regeneration is selected from 2-propanol, 2-butanol, butan-1,4-diol, 2-pentanol, pentan-1,5-diol, 4-methyl-2-pentanol, 2-hexanol, hexan-1,5-diol, 2-heptanol, or 2-octanol, particularly 2-propanol.

Particularly useful is 2-propanol for the regeneration of the cofactor at the same enzyme also catalyzing the target reaction and the continuous removal of the acetone formed.

In one aspect of the invention, the oxidoreductase catalyzing the asymmetric reduction of a compound of formula (V) to a compound of formula (III) is a diastereoselective NADPH-dependent oxidoreductase.

In one aspect of the invention, the oxidoreductase catalyzing the asymmetric reduction of a compound of formula (V) to a compound of formula (III) is a diastereoselective NADPH-dependent oxidoreductase selected from the list of:

KRED-NADPH-111 (from Codexis Inc., Redwood City, Calif., USA),
KRED-NADPH-112 (from Codexis Inc., Redwood City, Calif., USA),
KRED-NADPH-113 (from Codexis Inc., Redwood City, Calif., USA),
KRED-NADPH-114 (from Codexis Inc., Redwood City, Calif., USA),
KRED-NADPH-115 (from Codexis Inc., Redwood City, Calif., USA),
KRED-NADPH-121 (from Codexis Inc., Redwood City, Calif., USA),
KRED-NADPH-123 (from Codexis Inc., Redwood City, Calif., USA),
KRED-NADPH-145 (from Codexis Inc., Redwood City, Calif., USA),
KRED-NADPH-155 (from Codexis Inc., Redwood City, Calif., USA),
A231 (from Almac Group Ltd. Craigavon, United Kingdom), and
KRED-NADPH-136 (from Enzysource, Hangzhou, China).

Further suitable oxidoreductase catalyzing the asymmetric reduction of a compound of formula (V) to a compound of formula (III) are diastereoselective NADPH-dependent oxidoreductase selected from the list of:

KRED-X1, an engineered ketoreductase from *Lactobacillus kefir* as disclosed in PCT Int. Publication No. WO2010/025238A2 and identified as SEQ. ID. NO. 34, and KRED-X2, an engineered ketoreductase from *Sporobolomyces salmonicolor* as disclosed in PCT Int. Publication No. WO2009/029554A2 and identified as SEQ. ID. NO. 138.

Further suitable oxidoreductase catalyzing the asymmetric reduction of a compound of formula (V) to a compound of formula (III) are variants of KRED-X1 which are commercially available (from Codexis Inc., Redwood City, Calif., USA).

Particularly useful is the engineered ketoreductase "KRED-X1-P1B06", a KRED variant "P1B06" from the Codexis KRED specialty plate product "KRED-X1-SPECIALTY-PLT".

Further suitable oxidoreductase catalyzing the asymmetric reduction of a compound of formula (V) to a compound of formula (III) are variants of KRED-X1 which are commercially available (from Codexis Inc., Redwood City, Calif., USA). Particularly useful are the following engineered ketoreductases from the Codexis KRED specialty plate product "KRED-X1.1-B06-SPECIALTY-PLT":

"KRED-X1.1-P1F01" (KRED variant P1F01),
"KRED-X1.1-P1H10" (KRED variant P1H10),
"KRED-X1.1-P1G11" (KRED variant P1G11),
"KRED-X1.1-P1C04" (KRED variant P1C04),
"KRED-X1.1-P1C11" (KRED variant P1C11), and
"KRED-X1.1-P1C08" (KRED variant P1C08).

Particularly useful are the engineered ketoreductases "KRED-X1.1-P1C04" and "KRED-X1.1-P1F01". Most particular ketoreductase is the engineered ketoreductase "KRED-X1.1-P1F01".

PCT Int. Publications No. WO2010/025085A2 and WO2009/029554A2 are hereby incorporated by reference in their entirety for all purposes, particularly the aspects therein relating to the preparation and use of oxidoreductases.

All of the above mentioned enzymes might use as well the cofactor NADH.

In one particular aspect of the invention, the oxidoreductase catalyzing the asymmetric reduction of a compound of formula (V) to a compound of formula (III) is a diastereoselective NADPH-dependent oxidoreductase selected from the list of KRED-NADPH-111, KRED-NADPH-112, KRED-NADPH-113, KRED-NADPH-114, KRED-NADPH-115, KRED-NADPH-121, KRED-NADPH-123, KRED-NADPH-145, KRED-NADPH-155, A231, KRED-NADPH-136, KRED-X1, KRED-X2, KRED-X1-P1B06, KRED-X1.1-P1F01, KRED-X1.1-P1H10, KRED-X1.1-P1G11, KRED-X1.1-P1C04, KRED-X1.1-P1C11, and KRED-X1.1-P1C08.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1, KRED-X2, KRED-X1-P1B06, KRED-X1.1-P1F01, KRED-X1.1-P1H10, KRED-X1.1-P1G11, KRED-X1.1-P1C04, KRED-X1.1-P1C11, and KRED-X1.1-P1C08.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1, KRED-X2, KRED-X1-P1B06, KRED-X1.1-P1C04 and KRED-X1.1-P1F01.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1, KRED-X1-P1B06, KRED-X1.1-P1C04 and KRED-X1.1-P1F01.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1 and KRED-X2.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1 and KRED-X1-P1B06.

In one particular aspect of the invention, the oxidoreductase catalyzing the asymmetric reduction of a compound of formula (V) to a compound of formula (III) is a diastereoselective NADPH-dependent oxidoreductase selected from the list of KRED-X1.1-P1C04 and KRED-X1.1-P1F01.

In one particular aspect of the invention, the oxidoreductase catalyzing the asymmetric reduction of a compound of formula (V) to a compound of formula (III) is the diastereoselective NADPH-dependent oxidoreductase KRED-X1.1-P1F01.

In one aspect of the invention, the asymmetric reduction of a compound of formula (V) to a compound of formula (III) is performed in an aqueous medium in the presence of one or more organic cosolvents.

In one aspect of the invention, the asymmetric reduction of a compound of formula (V) to a compound of formula (III) is performed in an aqueous medium in the presence of one or more organic cosolvents, wherein the organic cosolvents are present in a total concentration from 1 to 50% V, particularly from 4 to 40% V.

In one aspect of the invention, the cosolvents present in the asymmetric reduction of a compound of formula (V) to a compound of formula (III) are selected from the list of glycerol, 2-propanol, diethylether, tert.butylmethylether, diisopropylether, dibutylether, methyl tetrahydrofurane, ethylacetate, butylacetat, toluene, heptane, hexane, cyclohexene and mixtures thereof; particularly 2-propanol.

2-propanol is particularly useful as cosolvent as it can serve as final reductant for the substrate coupled cofactor regeneration.

In one aspect of the invention, the asymmetric reduction of a compound of formula (V) to a compound of formula (III) is performed at a reaction temperature between 1° C. and 50° C., particularly between 20° C. and 45° C.

Temperatures in the upper range increase the reaction rate and facilitate the acetone removal.

In one aspect of the invention, the asymmetric reduction of a compound of formula (V) to a compound of formula (III) is performed at a pH between 5.5 and 8.5.

In one aspect of the invention, the asymmetric reduction of a compound of formula (V) to a compound of formula (III) is performed in an aqueous buffer. Suitable buffers are known to the specialist in the art. Particular buffer are 2-(N-morpholino)ethanesulfonic acid (MES) or potassium dihydrogen phosphate (PBS).

The optimal pH range and therefore any suitable buffers are depending on the particular oxidoreductase employed.

One aspect of the invention relates to the asymmetric reduction of a compound of formula (V) to a compound of formula (III), wherein the compound of formula (V) is initially present at a concentration of 1 to 25% wt, particularly 10 to 20% wt.

One aspect of the invention relates to the asymmetric reduction of a compound of formula (V) to a compound of formula (III), wherein the reaction concentration (total concentration of ketone of formula (V) and chiral alcohol of formula (III) in the reaction mixture) is between 1 and 25% wt, particularly between 10 and 20% wt.

One aspect of present invention relates to the process for the manufacture of compounds of formula (III) comprising the asymmetric reduction of the compound of formula (V) catalyzed by an oxidoreductase followed by work up by extraction or by filtration.

One aspect of the invention relates to the asymmetric reduction of a compound of formula (V) to a compound of formula (III) catalyzed by an oxidoreductase, wherein the product is conventionally worked up by extraction or by filtration.

The crude product purity might be further increased by crystallization or used as is in the subsequent reaction sequence for the manufacture of compounds of formula (I).

One aspect of present invention relates to the process for the manufacture of compounds of formula (III) comprising the asymmetric reduction of the compound of formula (V) catalyzed by an oxidoreductase, followed by work up by extraction or by filtration and further by crystallization.

One aspect of the invention relates to the asymmetric reduction of a compound of formula (V) to a compound of formula (III), wherein the product is conventionally worked up by extraction or by filtration and further by crystallization.

One aspect of the present invention relates to the process for the manufacture of compounds of formula (IVc):

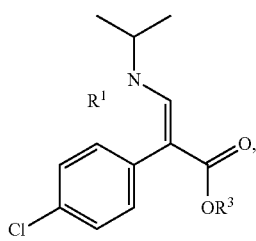

(IVc)

or a salt thereof, wherein R¹ and R³ are defined herein, comprising contacting a compound of formula (IVd):

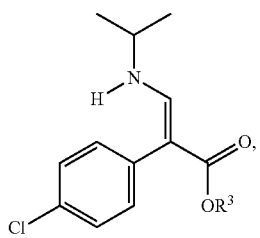

(IVd)

or a salt thereof, with R¹—X, wherein X is a leaving group, under conditions sufficient to give a compound of formula IVc or a salt thereof.

In one embodiment, the process comprises manufacturing ethyl (E)-3-(tert-butoxycarbonyl(isopropyl)-amino)-2-(4-chlorophenyl)acrylate, or a salt thereof, wherein R¹ is BOC protecting group, R³ is ethyl, and wherein R¹—X is $(BOC)_2O$.

In one particular embodiment, the process comprises contacting a compound of formula IVd or a salt thereof with less than about 8 equivalents of $(BOC)_2O$, particularly less than about 4 equivalents, more particularly about 3 equivalents under conditions that give a compound of formula IVc or a salt thereof in yields of greater than about 50%, particularly about 75% or more yield, in a polar solvent mixture comprising DMF.

In one more particular embodiment, the conditions comprise contacting a compound of formula IVd or a salt thereof with about 3 equivalents $(BOC)_2O$, and a basic mixture comprising about 2 equivalents each of tributylamine and dimethylaminopyridine (DMAP), in a polar solvent mixture comprising DMF. In an embodiment, the process further comprises removing a portion of the liquid from the reaction mixture under vacuum during the addition of the $(BOC)_2O$.

Compounds of formula (V) can be prepared according to methods known to those skilled in the art. A particular general method of preparation of compounds of formula (V) is depicted in Scheme 3. For a more detailed description of the individual reaction steps, see the Examples section below.

Scheme 3

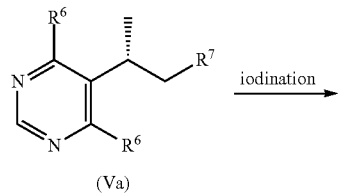

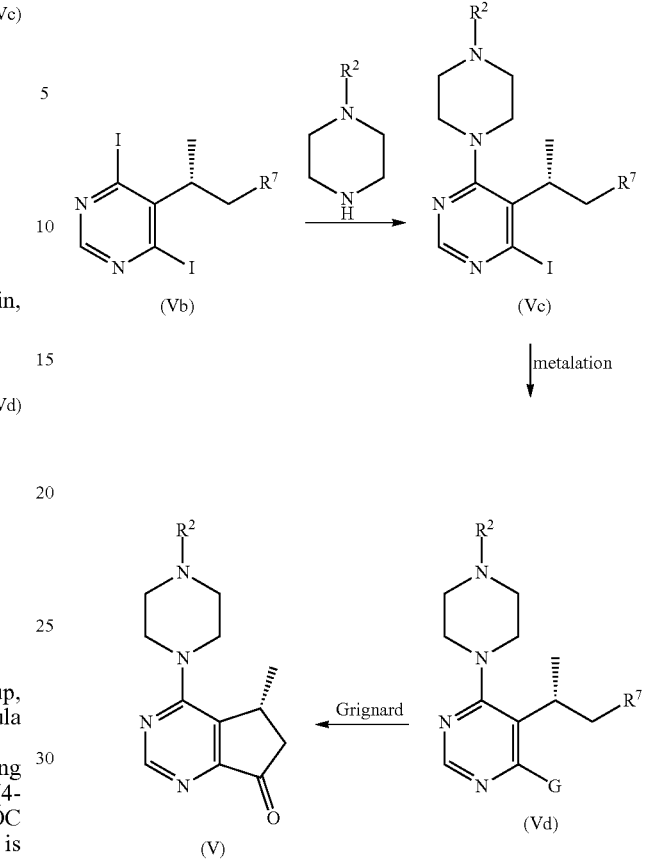

The reaction of a compound of formula (Va) with an iodination agent (e.g. iodide salt, such as NaI and optionally with an acid) gives a diiodopyrimidine of formula (Vb), which can be further reacted with a mono-protected piperazine to afford a compound of formula (Vc). The compound of formula (Vc) is metalated with a metalating agent, such as a Grignard reagent (e.g. a $C_{1-7}$ alkylmagnesium halide, such as iPrMgCl) to form a compound of formula (Vd) which is further cyclized to form a cyclopentyl ketone of formula (V), wherein R² is as described herein, G is Li or Mg, R⁶ is Cl or OH, R⁷ is —CN, —COOR$^a$ or —CONR$^a$R$^b$, wherein R$^a$ and R$^b$ are independently selected from the list of hydrogen, —OH, $C_{1-7}$ alkoxy, $C_{1-7}$ alkyl, $C_{2-7}$ alkenyl, $C_{2-7}$ alkynyl, $C_{3-8}$ cycloalkyl, phenyl or 3 to 12 membered heterocycloalkyl; or R$^a$ and R$^b$ are taken together with the nitrogen atom to which they are attached to form a 3-7 membered heterocycloalkyl.

WO 2008/006040 discloses methods of manufacture of compounds of formula (73, wherein compounds of formula (71) after deprotection using an acid are acylated with the appropriate amino acid, wherein R and R⁵ can have various alternatives.

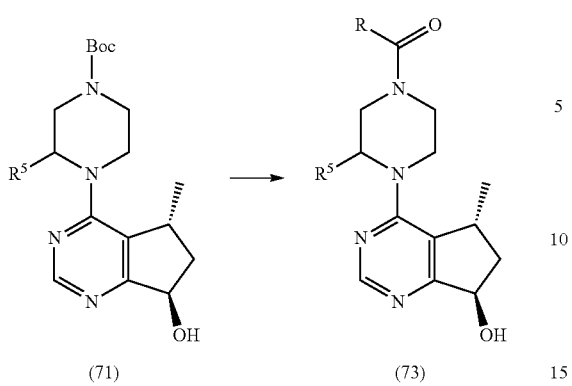

(71)  (73)

The acylation reactions as described in prior art exhibit the following drawbacks:

- A process employing HBTU as coupling reagent is not suited for a large scale commercial manufacturing process. HBTU raises severe industrial hygiene concerns as cases of anaphylaxis and occupational allergic contact dermatitis are described in literature (Hannu T et al, *Occup Med,* 2006, 56 (6), 430-433 and M A. Aleer et al, *Contact Dermatitis,* 2010 62, 2 123).
- A process employing dichloromethane as solvent is not suited for a large scale commercial manufacturing process since it is classified as hazardous air pollutant (HAP) in the US. Furthermore, dicholoromethane it is rated by the International Conference on Harmonisation (ICH) as class 2 solvent with a tight permitted daily exposure (PDE) due to its inherent toxicity.
- Purification of a product using chromatography is not an acceptable purification method for bulk scale small molecule manufacturing due to its very high solvent consumption and low throughput.
- In case a commercial bulk scale reaction process involves more than one solvent in a mixture, the solvents require distinct boiling points sufficiently apart from each other in order to allow separation from each other and recyclation using distillation. Processes, involving in the same step four solvents (e.g. with cyclopentyl methyl ether (CPME)) which are not recyclable because the mixture is inseparable, are not suited for large scale manufacturing.
- Work-up of products requiring numerous (e.g. six) aqueous extractions, all of them with concentrated inorganic salts, result in significant amounts of contaminated waste water. Such process conditions result in environmentally disadvantageous production process.

Inventors of present invention have discovered a new improved process for the manufacture of a compound of formula (I), which comprises the coupling of a compound of formula (II), which is a salt particularly a sodium salt, to a compound of formula (III). It has been found, that the use of the compound of formula (II) as salt, particularly a sodium salt, facilitates and simplifies such process substantially, as compared to the use of a free amino acid.

The process for the manufacture of compounds of formula (I) according to the invention features a number of relevant advantages as compared to processes described in the art, amongst others e.g.:

- The work-up of the compound of formula (I) is considerably improved. Only three solvents (isopropanol, toluene and heptane) are employed which are well separable.
- Propylphosphonic anhydride (T3P) is a non-toxic coupling agent with no allergenic and sensitizing properties.
- By-products of the reaction are water soluble and can therefore readily be removed by e.g. three-fold aqueous extraction.

One aspect of present invention provides a process for the preparation of a compound of formula (I)

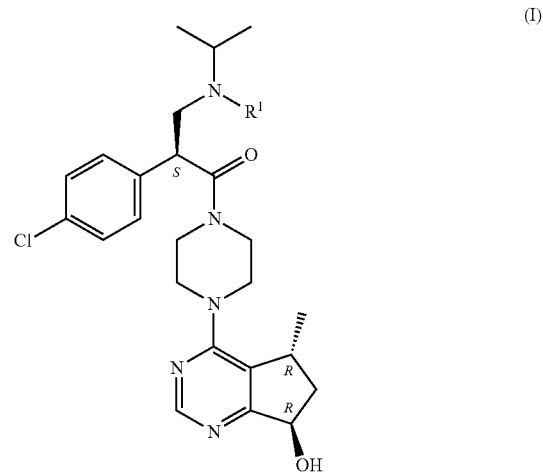

or salts thereof, which comprises the coupling reaction of a compound of formula (II)

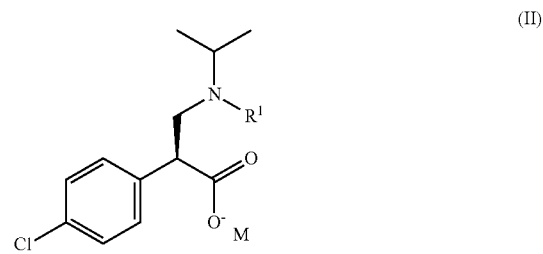

with a compound of formula (III)

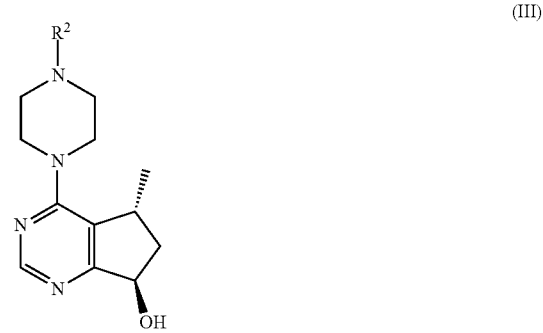

wherein $R^1$, $R^2$ and M are as defined herein.

One aspect of present invention provides a process for the preparation of a compound of formula (I) or salts thereof, which comprises the coupling reaction of a compound of formula (II) with a compound of formula (III) wherein R¹, R² and M are as defined herein, comprising the following reaction steps:

a) Deprotection of the compound of formula (III) in a solvent under acidic conditions;
b) adjustment to an alkaline pH using a base;
c) Addition of a solution comprising the compound of formula (II) in a solvent;
d) Addition of a solution comprising a coupling agent in a solvent.

In one aspect of the invention, the deprotection in step a) is performed using hydrochloric acid, sulfuric acid, trifluoro acetic acid or hydrobromic acid.

In a particular aspect of the invention, the deprotection in step a) is performed using hydrochloric acid.

In one aspect of the invention, the solvent used for deprotection in step a) is selected from water, methanol, ethanol, n-propanol, isopropanol, n-butanol, and tert-butanol.

In a particular aspect of the invention, the solvent used for deprotection in step a) is selected from n-propanol or isopropanol.

In one aspect of the invention, the deprotection in step a) is performed at a temperature from 50 to 100° C., particularly at 80° C.

In one aspect of the invention, the deprotection in step a) is performed during a reaction time of 0.1 to 24 hours, particularly during a reaction time of 1 to 2 hours.

In one aspect of the invention, the base in step b) is a liquid base selected from N-ethyl morpholine (NEM), triethylamine (TEA), tri(n-propyl)amine (TPA), diisopropylethylamine (DIPEA), pyridine and lutidine.

In one aspect of the invention, the base in step b) is N-ethyl morpholine (NEM).

In one aspect of the invention, in step b) 4 to 8 equivalents of base are added in relation to the compound of formula (III), particularly 6 to 7 equivalents of base, most particularly 6.5 equivalents of base.

In one aspect of the invention, the solvent used in step c) is identical to the solvent used in step a).

In one aspect of the invention, the solvent used in step c) is selected from water, methanol, ethanol, n-propanol, isopropanol, n-butanol, and tert-butanol.

In a particular aspect of the invention, the solvent in step c) is selected from n-propanol or isopropanol.

In one aspect of the invention, the coupling agent used in step d) is propylphosphonic anhydride (T3P).

In one aspect of the invention, the solvent used in step d) is selected from methanol, ethanol, n-propanol, isopropanol, n-butanol, tert-butanol, toluene, acetonitrile, tetrahydrofuran, N,N-dimethylformamide, chloroform, methylene chloride, dichloromethane, dichloroethane, diethyl ether, acetone, methyl ethyl ketone, dimethyl sulfoxide, N,N-dimethyl acetamide, N-methyl pyrrolidinone, dioxane, tetrahydropyran, pyridine, 2-propanone, 2-butanone, ethylene glycol dimethyl ether, ethyl acetate, butyl acetate, isopropyl acetate, and mixtures of above.

In a particular aspect of the invention, the solvent used in step d) is selected from a mixture of n-propanol and toluene or isopropanol and toluene, most particularly a mixture of n-propanol and toluene.

In one aspect of the invention, the coupling reaction in step d) is performed at a temperature from −10 to 50° C., particularly from 0 to 25° C.

In one aspect of the invention, the coupling reaction in step d) is performed during a reaction time of 0.1 to 24 hours, particularly during a reaction time of 1 to 4 hours.

One aspect of present invention relates to the coupling reaction of a compound of formula (II) with a compound of formula (III), wherein after step d) the product is worked up by aqueous extraction.

In a particular aspect of the invention, the work up of the product after step d) comprises one to six extractions with water, particularly three extractions with water.

One aspect of present invention relates to the process for the manufacture of compounds of formula (VI)

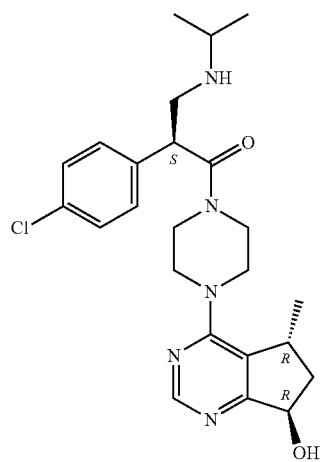

(VI)

or pharmaceutically acceptable salts thereof, wherein a compound of formula (I) is deprotected

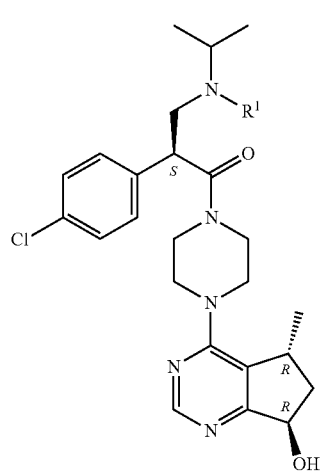

(I)

wherein R¹ is as defined herein.

One aspect of present invention relates to the process for the manufacture of compounds of formula (VI) or pharmaceutically acceptable salts thereof, wherein a compound of formula (I) is deprotected, wherein R¹ is as defined herein, comprising the following reaction steps:

i) Deprotection of the compound of formula (I) in a solvent under acidic conditions;
ii) Adjustment of the pH using a base in a solvent;
iii) Optionally crystallizing the compound of formula (VI).

In one aspect of the invention, the deprotection in step i) is performed using hydrochloric acid, sulfuric acid, trifluoro acetic acid or hydrobromic acid.

In a particular aspect of the invention, the deprotection in step i) is performed using hydrochloric acid.

In one aspect of the invention, the solvent used for deprotection in step i) is selected from water, methanol, ethanol, n-propanol, isopropanol, and tert-butanol or mixtures thereof.

In a particular aspect of the invention, the solvent used for deprotection in step i) is selected from n-propanol, isopropanol and a 1:1 mixture of n-propanol/water.

In one aspect of the invention, the deprotection in step i) is performed at a temperature from 30 to 100° C., particularly at 80° C.

In one aspect of the invention, the deprotection in step i) is performed during a reaction time of 1 to 24 hours, particularly during a reaction time of 1 to 4 hours.

In one aspect of the invention, the base in step ii) is NaOH in a 1:1 mixture of n-propanol/water.

In one aspect of the invention, the base in step ii) is ammonia.

In one aspect of the invention, the solvent used in step ii) is identical to the solvent used in step i).

In one aspect of the invention, the solvent used in step ii) is selected from water, methanol, ethanol, n-propanol, isopropanol, n-butanol, and tert-butanol or mixtures thereof.

In a particular aspect of the invention, the solvent in step ii) is selected from n-propanol, isopropanol and a 1:1 mixture of n-propanol/water.

In a particular aspect of the invention, the adjustment of the pH is performed by dropwise addition of a solution of ammonia (2-4% wt, particularly 3.8% wt) in isopropanol or of a solution of NaOH (5-10M, particularly 7M) in a 1:1 mixture of n-propanol/water.

In a particular aspect of the invention, the final pH after adjustment in step ii) is above pH 6, particularly between pH 6 and 7.

In one aspect of the invention, the crystallization in step iii) is performed by a solvent switch to a crystallization solvent suitable for crystallization of the compound of formula (VI).

In a particular aspect of the invention, the crystallization solvent in step iii) is selected from toluene, heptane, tetrahydrofuran, 2-propanone, 2-butanone, ethylene glycol dimethyl ether, ethyl acetate, butyl acetate, isopropyl acetate and mixtures thereof.

In a particular aspect of the invention, the crystallization solvent in step iii) is ethyl acetate.

One aspect of the invention relates to compounds obtainable by any process as described herein.

One aspect of the invention relates to pharmaceutical compositions comprising compounds obtainable by any process as described herein.

One aspect of the invention relates to a compound of formula (VI) as described herein comprising between 1 ppb and 100 ppm of the compound of formula (I), wherein $R^1$ is as defined herein.

One aspect of the invention relates to a compound of formula (VI) as described herein comprising between 1 ppb and 1 ppm of the compound of formula (I), wherein $R^1$ is as defined herein.

One aspect of the invention relates to a pharmaceutical composition comprising compounds of formula (VI) as described herein.

One aspect of the invention relates to a compound of formula (I) as described herein comprising between 1 ppb and 100 ppm of the compound of formula (II), wherein $R^1$ and M are as defined herein.

One aspect of the invention relates to a compound of formula (I) as described herein comprising between 1 ppb and 1 ppm of the compound of formula (II), wherein $R^1$ and M are as defined herein.

One aspect of the invention relates to a compound of formula (I) as described herein comprising between 1 ppb and 100 ppm of the compound of formula (III), wherein $R^1$ and $R^2$ are as defined herein.

One aspect of the invention relates to a compound of formula (I) as described herein comprising between 1 ppb and 1 ppm of the compound of formula (III), wherein $R^1$ and $R^2$ are as defined herein.

One aspect of the invention relates to a compound of formula (I) as described herein comprising between 1 ppb and 100 ppm of the compound of formula (II) and between 1 ppb and 100 ppm of the compound of formula (III), wherein $R^1$, $R^2$ and M are as defined herein.

One aspect of the invention relates to a compound of formula (I) as described herein comprising between 1 ppb and 1 ppm of the compound of formula (II) and between 1 ppb and 1 ppm of the compound of formula (III), wherein $R^1$, $R^2$ and M are as defined herein.

EXAMPLES

The following examples 1-15 are provided for illustration of the invention. They should not be considered as limiting the scope of the invention, but merely as being representative thereof.

Example 1

(E)-3-(tert-butoxycarbonyl(isopropyl)amino)-2-(4-chlorophenyl)acrylic acid

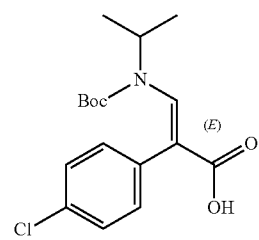 [SMILES: CC(C)N(/C=C(/C(=O)O)c1ccc(Cl)cc1)C(=O)OC(C)(C)C]

Into a solution of ethyl formate (123.9 L, 1538.9 mol) in MTBE (189 L) was added ethyl 4-chlorophenylacetate (120 kg, 604.1 mol). The mixture was stirred at 15-30° C. for 30 min and then a mixture of t-BuOK (136.8 kg, 1219.1 mol) in MTBE (1215.8 L) was added while maintaining the internal temperature below 5° C. The mixture was stirred between 0-10° C. for 1.5 h. The reaction mixture was added to an aqueous solution of hydrochloric acid (35%, 99.8 L in 560 L $H_2O$) maintaining the internal temperature below 10° C. The mixture was stirred for 30 min between 0-10° C. until a final pH=2 was observed. The layers were separated and the organic layer was washed with 25% NaCl solution (496 L).

The mixture was cooled to −5° C. and then isopropylamine (107.2 L, 1251.9 mol) and AcOH (70.5 L, 1233.3 mol) were slowly added maintaining the temperature <10° C. The mixture was stirred for 3 h at 0-10° C. and then the organic layer was washed with $H_2O$ (760 L), 15% aqueous $Na_2CO_3$ (424 L) and then 25% aqueous NaCl (650 L). The aqueous layer was separated and DMF (443 L) and DMAP (14.4 kg, 117.9 mol) were added to the organic solution. The mixture was then heated to 60-65° C. followed by slow addition of (Boc)₂O (951.6 L, 4142 mol), DMF (228.6 L) and triethylamine (263.0 L, 1821.8 mol) over 24 h. After stirring ~6 h, the mixture was cooled to room temperature and MTBE (1434 L), water (1010 L) and 10% aqueous citric acid (938 L) were added. The aqueous layer was separated and the mixture was washed by 25% aqueous NaCl (984 L). The organic layer was then concentrated via distillation to a minimum working volume (~240 L) while maintaining the temperature below 50° C. The organic layer was then stirred for 5 h at 0-5° C. and filtered. The filter cake was washed with heptane (20.6 L) and dried to afford (E)-ethyl 3-((tert-butoxycarbonyl)(isopropyl)amino)-2-(4-chlorophenyl)acrylate (148.55 kg, 63% yield over three steps) as a white solid.

(E)-ethyl 3-((tert-butoxycarbonyl)(isopropyl)amino)-2-(4-chlorophenyl)acrylate (133.5 kg, 362.9 mol) was added into a mixture of H₂O (252 L), NaOH (58.25 kg, 1456 mol) and EtOH (383.5 L) stirred at room temperature. The mixture was warmed to 40-45° C. for 2.5 h until a clear solution was formed. The mixture was concentrated to a minimum working volume maintaining the temperature below 50° C. The mixture was then cooled to 10-25° C. and a solution of HCl was added (842 L of 2N HCl and 11 L of 35% HCl) until a final pH=2-4 was obtained. The aqueous layer was separated and the organic layer was washed with 25% aqueous NaCl (810 L). n-heptane was added while distilling to form a suspension. The product was collected and washed with n-heptane and dried at 40-45° C. for ~10 h to afford 110.7 kg (90.5% yield) of (E)-3-(tert-butoxycarbonyl(isopropyl)amino)-2-(4-chlorophenyl)acrylic acid having 99.9% purity by HPLC. E-configuration was confirmed using single crystal x-ray analysis.

Example 1a (E)-ethyl 3-((tert-butoxycarbonyl)-(isopropyl) amino)-2-(4-chlorophenyl)acrylate

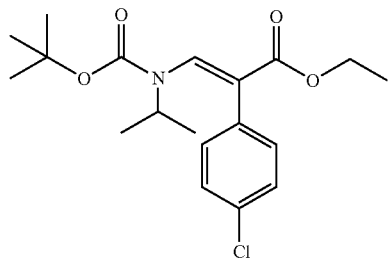 [SMILES: CCOC(=O)/C(=C/N(C(=O)OC(C)(C)C)C(C)C)c1ccc(Cl)cc1]

To a concentrated solution of ethyl 2-(4-chlorophenyl)-3-(isopropylamino)acrylate (prepared as above in Example 1 from 120 kg ethyl 2-(4-chlorophenyl)acetate, 0.604 kmol) was added DMF (354 kg) and the batch was concentrated to 3 volumes. DMAP (14.0 kg, 114.6 mol) and n-Bu₃N (224.21 kg, 1.21 kmol) were added and the mixture was heated to 70-75° C. and a solution of (BOC)₂O (330 kg, 1.51 kmol) in DMF (169 kg) solution was added over 2 h at 70-75° C. After the addition was complete about 200 L DMF was removed under vacuum over 3 h below 75° C. Addition of (BOC)₂O (68.6 kg, 0.314 kmol) in DMF (32.4 kg) solution was continued over 0.5 h at 70-75° C. After the addition was complete, the batch was concentrated at a temperature below 75° C. and then cooled to about 23.5° C. MTBE (899.6 kg) was charged and then the mixture was cooled to about 12.6° C. Citric acid monohydrate (197.4 kg) in water (702 kg) solution was added at 10-20° C. The layers were separated and the organic layer was washed with 5% aqueous NaCl (582 kg). The layers were cut and the organic layer was concentrated to 240-360 L at below 50° C. After n-heptane (77 kg) was charged, the mixture was concentrated to 240-360 L at below 50° C. After n-heptane (70 kg) was charged, the suspension was stirred for 4 h at 0-10° C. and the product was collected by centrifugation. The cake was washed with n-heptane (28.2 kg) and (E)-ethyl 3-((tert-butoxycarbonyl)(isopropyl)amino)-2-(4-chlorophenyl)acrylate was obtained (170.6 kg, 77% yield, 99.8 A % HPLC), which can be used as above in this Example 1 to prepare (E)-3-(tert-butoxycarbonykisopropyl)amino)-2-(4-chlorophenyl)acrylic acid.

Example 2

Sodium (S)-3-(tert-butoxycarbonyl(isopropyl) amino)-2-(4-chlorophenyl)propanoate

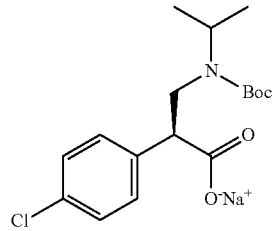

In a glove box (O₂ content≤2 ppm), a 50 ml autoclave was charged with 6.8 g (20.0 mmol) of (E)-2-(4-chlorophenyl)-3-[(2-methylpropan-2-yl)oxycarbonyl-propan-2-ylamino] prop-2-enoic acid, 34 ml of ethanol and 4.81 mg (0.0051 mmol, S/C 4'000) of [Ru(TFA)₂((S)-BINAP]. The asymmetric hydrogenation was run for 7 h at 60° C. under 18 bar of hydrogen. After cooling to room temperature the pressure was released from the autoclave and a sample of the yellow reaction solution was analyzed to show >99% conversion to (S)-3-(tert-butoxycarbonyl-isopropyl-amino)-2-(4-chlorophenyl)-propionic acid with a S/R enantiomeric ratio of 99.3 to 0.7. The hydrogenation mixture was transferred with aid of 100 ml of tert-butyl methyl ether into a 1 l glass reactor under argon which contained the crude reaction mixture of 6 analogous hydrogenation experiments (in total 47.9 g of (E)-2-(4-chlorophenyl)-3-[(2-methylpropan-2-yl)oxycarbonyl-propan-2-ylamino]prop-2-enoic acid), then an ethanol solution of sodium ethoxide (52.3 ml, 140 mmol) was added dropwise at 50° C. under stirring. A yellowish precipitate formed which was stirred at the same temperature and then at room temperature over night. The precipitated product was filtered off, washed with a t-butyl methyl ether/ethanol 4:1 mixture (300 ml) and with t-butyl methyl ether (200 ml), dried under vacuum until weight constancy to yield sodium (S)-3-(tert-butoxycarbonyl(isopropyl)amino)-2-(4-chlorophenyl)propanoate in 96.3% yield (49.03 g) and with a S/R enantiomeric ratio of >99.9 to <0.1% as white crystals. ¹H-NMR (D₂O): δ 7.32 (d, 2H), 7.22 (d, 2H), 3.65-3.85 two bs, aryl-CH and N—CH(CH₃)₂), 3.55 (m, 2H), 1.29 (s, 9H), 1.00 (d, 3H), 0.80 (bs, 3H).

The enantiomeric ratio was determined by HPLC using a Chiralpak-AD-3 column, 150 mm*4.6 mm. Eluents: A) n-heptane with 0.10% trifluoracetic acid, B) ethanol, flow: 1.25 ml/min, 25° C., 5 μl injection volume, 220 nm. Retention times: (S)-3-(tert-Butoxycarbonyl-isopropyl-amino)-2-(4-chloro-phenyl)-propionic acid 2.48 min, (R)-3-(tert-Butoxycarbonyl-isopropyl-amino)-2-(4-chloro-phenyl)-propionic acid 2.77 min, (E)-2-(4-chlorophenyl)-3-[(2-methylpropan-2-yl)oxycarbonyl-propan-2-ylamino]prop-2-enoic acid 3.16 min.

Example 3

Sodium (S)-3-(tert-butoxycarbonyl(isopropyl)amino)-2-(4-chlorophenyl)propanoate

In a glove box ($O_2$ content≤2 ppm), a 185 ml autoclave was charged with 17.0 g (50.0 mmol) of (E)-2-(4-chloro-phenyl)-3-[(2-methylpropan-2-yl)oxycarbonyl-propan-2-ylamino]prop-2-enoic acid, 70 ml of ethanol and 4.74 mg (0.005 mmol, S/C 10'000) of [Ru(TFA)$_2$((S)-BINAP]. The asymmetric hydrogenation was run for 22 h at 70° C. under 18 bar of hydrogen. After cooling to room temperature the pressure was released from the autoclave and a sample of the yellow reaction solution was analyzed to show >99% conversion to (S)-3-(tert-butoxycarbonyl-isopropyl-amino)-2-(4-chloro-phenyl)-propionic acid with a S/R enantiomeric ratio of 98.2 to 1.8. The hydrogenation mixture was transferred with aid of 200 ml of tert-butyl methyl ether into a 400 ml glass reactor under argon then an ethanol solution of sodium ethoxide (18.7 ml, 50 mmol) was added dropwise at 50° C. under stirring. A yellowish precipitate formed which was stirred at the same temperature and then at room temperature for a total of 3.5 h. The precipitated product was filtered off, washed with a t-butyl methyl ether/ethanol 4:1 mixture (80 ml) and with t-butyl methyl ether (20 ml), dried under vacuum until weight constancy to yield sodium (S)-3-(tert-butoxycarbonyl(isopropyl)amino)-2-(4-chlorophenyl)propanoate in 94.6% yield (17.35 g) and with a S/R enantiomeric ratio of 100 to 0% as white crystals.

Example 3a

Sodium (S)-3-(tert-butoxycarbonyl(isopropyl)amino)-2-(4-chlorophenyl)propanoate

In a glove box ($O_2$ content≤2 ppm), a 185 ml autoclave was charged with 10.0 g (29.4 mmol) of (E)-2-(4-chloro-phenyl)-3-[(2-methylpropan-2-yl)oxycarbonyl-propan-2-ylamino]prop-2-enoic acid, 125 ml of ethanol, 0.118 mL NaBr solution in water (1M) and 5.77 mg (0.006 mmol, S/C 5'000) of [Ru(TFA)$_2$((S)-BINAP]. The asymmetric hydrogenation was run for 22 h at 60° C. under 18 bar of hydrogen. After cooling to room temperature the pressure was released from the autoclave and a sample of the yellow reaction solution was analyzed to show >99% conversion to (S)-3-(tert-butoxycarbonyl-isopropyl-amino)-2-(4-chloro-phenyl)-propionic acid with a S/R enantiomeric ratio of 98 to 2. The hydrogenation mixture was transferred with aid of 10 mL ethanol to a 0.5 L reactor. The reaction mixture was evaporated at 45° C. in vacuo to a residual volume of 65 mL.

70 ml of tert-butyl methyl ether were added at 45° C. Then an ethanol solution of sodium ethoxide (11.4 g, 35 mmol) was added dropwise at 45° C. under stirring. The funnel was rinsed with 1.3 g ethanol. A yellowish precipitate formed which was stirred at the same temperature for 1 h and then at room temperature for 1 h. The precipitated product was filtered off, washed with a t-butyl methyl ether/ethanol 1:1 mixture (13.6 g) and with t-butyl methyl ether (16 g), dried under vacuum until weight constancy to yield sodium (S)-3-(tert-butoxycarbonyl(isopropyl)amino)-2-(4-chlorophenyl)propanoate in 89% yield (9.52 g) and with with a S/R enantiomeric ratio of 100 to 0% as white crystals.

Example 3b

Sodium (S)-3-(tert-butoxycarbonyl(isopropyl)amino)-2-(4-chlorophenyl)propanoate

In a glove box ($O_2$ content≤2 ppm), a 185 ml autoclave was charged with 10.0 g (29.4 mmol) of (E)-2-(4-chloro-phenyl)-3-[(2-methylpropan-2-yl)oxycarbonyl-propan-2-ylamino]prop-2-enoic acid, 120 ml of ethanol (distilled under Ar), 0.118 mL NaCl solution in water (1M) and 5.8 mg (0.006 mmol, S/C 5'000) of [Ru(TFA)$_2$((S)-BINAP]. The asymmetric hydrogenation was run for 12 h at 60° C. under 18 bar of hydrogen. After cooling to room temperature the pressure was released from the autoclave and a sample of the yellow reaction solution was analyzed to show >99% conversion to (S)-3-(tert-butoxycarbonyl-isopropyl-amino)-2-(4-chloro-phenyl)-propionic acid with a S/R enantiomeric ratio of 99 to 1. The hydrogenation mixture was transferred with aid of 10 mL ethanol to a 0.5 L reactor. The reaction mixture was evaporated at 45° C. in vacuo to a residual volume of 65 mL.

70 ml of tert-butyl methyl ether were added at 20° C. Then solution of sodium ethoxide (21% (m/m), 9.5 g, 29.4 mmol) in ethanol was added dropwise at 45° C. under stirring. The funnel was rinsed with 1.3 g ethanol. A precipitate formed which was stirred at the same temperature for 1 h and then at room temperature for 1 h. The precipitated product was filtered off, washed with a t-butyl methyl ether/ethanol 1:1 mixture (13.6 g) and with t-butyl methyl ether (16 g), dried under vacuum until weight constancy to yield sodium (S)-3-(tert-butoxycarbonyl(isopropyl)amino)-2-(4-chlorophenyl)propanoate in 89% yield (9.5 g) and with with a S/R enantiomeric ratio of 100 to 0% as white crystals.

Example 3c (S)-3-(tert-butoxycarbonyhisopropyl)amino)-2-(4-chlorophenyl)-propionic acid In a glove box ($O_2$ content≤2 ppm), a 185 ml autoclave was charged with 17.1 g (50.0 mmol) of (E)-2-(4-chloro-phenyl)-3-[(2-methylpropan-2-yl)oxycarbonyl-propan-2-ylamino]prop-2-enoic acid and 75 ml of ethanol. In a separate flask a mixture of 4.79 mg (0.005 mmol, S/C 10'000) of [Ru(TFA)$_2$((S)-BINAP] and 8.3 ml of ethanol was treated with 1.67 ml (0.10 mmol) of a 60 millimolar HCl solution in water, the resulting suspension was stirred for 30 min and then added to autoclave. After having sealed the autoclave the asymmetric hydrogenation was run for 12 h at 60° C. under 18 bar of hydrogen. After cooling to room temperature the pressure was released from the autoclave and a sample of the yellow reaction solution was analyzed to show 99.5% conversion to (S)-3-(tert-butoxycarbonyl-isopropyl-amino)-2-(4-chloro-phenyl)-propionic acid with a S/R enantiomeric ratio of 98.7 to 1.3.

Example 3d (S)-3-(tert-butoxycarbonyhisopropyl)amino)-2-(4-chlorophenyl)-propionic acid The procedure of example 3c was repeated using HBr as additive. The hydrogenation proceeded with 99.8% conversion, the desired (S)-acid was isolated in quantitative yield with a S/R enantiomeric ratio of 98.7:1.3.

Example 3e (S)-3-(tert-butoxycarbonyhisopropyl)amino)-2-(4-chlorophenyl)-propionic acid In a glove box ($O_2$ content≤2 ppm), a 185 ml autoclave was charged with 17.0 g (50.0 mmol) of (E)-2-(4-chlorophenyl)-3-[(2-methylpropan-2-yl)oxycarbonyl-propan-2-ylamino]prop-2-enoic acid and 75 ml of ethanol. In a separate flask a mixture of 9.59 mg (0.010 mmol, S/C 5'000) of [Ru(TFA)$_2$((S)-BINAP] and 9.8 ml of ethanol was treated with 0.20 ml (0.20 mmol) of a 1 molar HCl solution in water, the resulting suspension was stirred for 30 min and then added to autoclave. After having sealed the autoclave the asymmetric hydrogenation was run for 12 h at 60° C. under 18 bar of hydrogen. After cooling to room temperature the pressure was released from the autoclave and a sample of the yellow reaction solution was analyzed to show 99.7% conversion to (S)-3-(tert-butoxycarbonyl-isopropyl-amino)-2-(4-chloro-phenyl)-propionic acid with a S/R enantiomeric ratio of 99.0 to 1.0.

Example 3f (S)-3-(tert-butoxycarbonyhisopropyl)amino)-2-(4-chlorophenyl)-propionic acid The procedure of example 3f was repeated using LiBr as additive. The hydrogenation proceeded with 98.9% conversion, the desired (S)-acid was isolated in quantitative yield with a S/R enantiomeric ratio of 98.5:1.5.

Example 4

(S)-3-(tert-butoxycarbonyhisopropyl)amino)-2-(4-chlorophenyl)-propionic acid

In a glove box ($O_2$ content≤2 ppm), a 35 ml autoclave equipped with a glass insert and a magnetic stirring bar was charged with 400 mg (1.18 mmol) of (E)-2-(4-chlorophenyl)-3-[(2-methylpropan-2-yl)oxycarbonyl-propan-2-ylamino]prop-2-enoic acid, 5.92 mg (0.00589 mmol) of [Ru(TFA)$_2$((S)-BINAP)] (S/C 200) and 4 ml of ethanol. The autoclave was sealed and pressurized with 20 bar of hydrogen, the asymmetric hydrogenation was run under stirring for 14 hours at 60° C. After cooling to room temperature the pressure was released from the autoclave, the ethanol solution was evaporated in vacuo to give (S)-3-(tert-Butoxycarbonyl-isopropyl-amino)-2-(4-chloro-phenyl)-propionic acid in quantitative yield and with an S/R enantiomeric ratio of 99:1. The conversion was >=99.9%.

Example 5.1 to 5.17(S) or (R)-3-(tert-butoxycarbonyl(isopropyl)amino)-2-(4-chlorophenyl)propionic acid The procedure of Example 4 was repeated using different chiral ruthenium catalysts to produce corresponding (R) and (S) isomers of 3-(tert-Butoxycarbonyl-isopropyl-amino)-2-(4-chloro-phenyl)-propionic acid. The results are shown in Table 1, together with catalyst, % conversion and S/R enantiomeric ratio. Reaction scale was in all experiments (unless specifically indicated in a footnote) 400 mg, temperature was 60° C., hydrogen pressure was 20 bar at S/C ratio of 200, reaction time was 14 h. The reactor was a 35 ml autoclave. The indicated amount of additive is intended relative to the amount of metal catalyst.

TABLE 1

| Example | Catalyst | Conversion (%) | Ratio S:R |
|---|---|---|---|
| 5.1 | Ru(OAc)$_2$((S)-BINAP) | 100 | 96.5:3.5 |
| 5.2 | Ru(OAc)$_2$((S)-MeOBIPHEP) | 100 | 94.0:6.0 |
| 5.3 | Ru(TFA)$_2$((S)-BINAP) | 100 | 99.0:1.0 |
| 5.4 a) | [Ru((S)-BINAP)(AN)$_4$](BF$_4$)$_2$ | 99.6 | 98.4:1.6 |
| 5.5 | Ru(OAc)$_2$((S)-2-Furyl-MeOBIPHEP) | 54 | 91.2:8.8 |
| 5.6 b) | RuCl$_2$((S)-pTol-BINAP)(S,S-DPEN) | 61 | 99.0:1.0 |
| 5.7 b) | Ru(TFA)$_2$((S)-TMBTP) | 100 | 98.4:1.6 |
| 5.8 b) | Ru(TFA)((S,S)-iPr-DUPHOS) | 50 | 13.3:86.7 |
| 5.9 b) | Ru(TFA)$_2$((R)-3,5-Xyl-BINAP) | 99.9 | 1.5:98.5 |
| 5.10 | Ru(TFA)$_2$((S)-BIPHEMP) | 100 | 99.3:0.8 |
| 5.11 | [Ru((R)-BINAP)(pCym)(AN)](BF$_4$)$_2$ | 99.8 | 1.6:98.4 |
| 5.12 c) | [RuCl((S)-BINAP)(C$_6$H$_6$)]BF$_4$ | 99.3 | 98.9:1.1 |
| 5.13 | [RuI((S)-BINAP)(C$_6$H$_6$)]I | 77 | 98.8:1.1 |
| 5.14 | [RuBr((S)-BINAP)(C$_6$H$_6$)]Br | 100 | 98.9:1.1 |
| 5.15 | [Ru(OAc)$_2$((S)-BINAP)]AlCl$_3$ | 100 | 98.5:1.5 |
| 5.16 | [RuCl((S)-BINAP)(C$_6$H$_6$)]Cl | 100 | 99.1:0.9 |
| 5.17 d) | Ru(TFA)$_2$((S)-BINAPHANE) | 100 | 2.0:98.0 | a) 35 ml autoclave, 1.7 g scale; S/C 250, 22 h.
b) 1.7 g scale, S/C 250, 14 h;
c) 6.8 g substrate in 50 ml autoclave, S/C 1500, 5 h.
d) Catalyst prepared in situ by stirring 2.56 mg [Ru(COD)(TFA)$_2$]$_2$ and 2.2 molar equivalents of chiral diphosphine in a glove box in 3 ml of ethanol for 3 h at 50° C.

Example 6.1 to 6.8

(S) or (R)-3-(tert-butoxycarbonyl(isopropyl)amino)-2-(4-chlorophenyl)propionic acid In an analogous manner to Examples 5.1-5.16 the following hydrogenations were performed using various substances as additives to afford the (R) and (S) isomers of 3-(tert-Butoxycarbonyl-isopropyl-amino)-2-(4-chloro-phenyl)-propionic acid in the purity and enantiomeric purity indicated in Table 2. Reaction scale was in all experiments (unless specifically indicated in a footnote) 400 mg, temperature was 60° C., hydrogen pressure was 18-20 bar during 4 h at S/C ratio of 200. The reactor was a 35 ml autoclave. The indicated amount of additive is intended relative to the amount of metal catalyst.

TABLE 2

| Example. | Catalyst | additive (amount) | Conversion (%) | Ratio S:R |
|---|---|---|---|---|
| 6.1 a) | Ru(OAc)$_2$((S)-BINAP) | LiBF$_4$ (20) | 100 | 98.1:1.9 |
| 6.2 | Ru(OAc)$_2$((S)-2-Furyl-MeOBIPHEP) | HBF$_4$ (4) | 26 | 92.8:7.2 |
| 6.3 | Ru(OAc)$_2$((S)-MeOBIPHEP) | HBF$_4$ (2) | 99.5 | 98.0:2.0 |
| 6.4 | Ru(OAc)$_2$((S)-BINAP) | HBF$_4$ (2) | 100 | 98.8:1.2 |
| 6.5 | Ru(TFA)$_2$((S)-BINAP) | HBF$_4$ (1) | 100 | 98.2:1.8 |

TABLE 2-continued

| Example. | Catalyst | additive (amount) | Conversion (%) | Ratio S:R |
|---|---|---|---|---|
| 6.6 | Ru(OAc)$_2$((S)-BINAP) | HCl (2) | 100 | 98.6:1.4 |
| 6.7 b) | Ru(TFA)$_2$((S)-BINAP) | H$_2$SO$_4$ (1) | 99.3 | 99.3:0.7 |
| 6.8 b) | Ru(TFA)$_2$((S)-BINAP) | CH$_3$SO$_3$H (1) | 99.5 | 99.4:0.6 |
| 6.9 c) | Ru(TFA)$_2$((S)-BINAP) | LiCl | >99 | 97.9:2.1 |
| 6.10 c) | Ru(TFA)$_2$((S)-BINAP) | LiBr | >99 | 98.6:1.4 |
| 6.11 c) | Ru(TFA)$_2$((S)-BINAP) | LiI | 49.5 | 98.6:1.4 |

For a) Reaction time 14 h; b) S/C 4000, 18 h, 6.8 g scale in a 185 ml autoclave; c) S/C 200, 14 h, 1.18 g scale, 30 ml autoclave, 20 bar H$_2$.

Example 7.1 to 7.11

(S) or (R)-3-(tert-butoxycarbonyl(isopropyl)amino)-2-(4-chlorophenyl)propionic acid The procedure of Examples 5.1-5.16 was repeated but the reaction conditions were varied in terms of hydrogen pressure, concentration and solvent to produce corresponding (R) and (S) isomers of 3-(tert-Butoxycarbonylsopropylamino)-2-(4-chloro-phenyl)-propionic acid. The results are shown in Table 3, Reaction scale was in all experiments (unless specifically indicated in a footnote) 400 mg in 4 ml of solvent, temperature was 60° C. at S/C ratio of 200, reaction time was 14 h. The reactor was a 35 ml autoclave, the catalyst was Ru(TFA)$_2$((S)-BINAP).

TABLE 3

| Example. | P H$_2$ (bar) | Solvent | Conversion (%) | Ratio S:R |
|---|---|---|---|---|
| 7.1 a) | 5 | EtOH | 99.8 | 98.8:1.2 |
| 7.2 a) | 40 | EtOH | 99.8 | 99.3:0.7 |
| 7.3 a) | 100 | EtOH | 99.8 | 98.5:1.5 |
| 7.4 | 20 | EtOH/H$_2$O 9:1 | 100 | 97.9:2.1 |
| 7.5 | 20 | EtOH/CH$_2$Cl$_2$ 1:1 | 99.8 | 98.8:1.2 |
| 7.6 | 20 | EtOH/EtOAc 1:1 | 99.8 | 98.5:1.5 |
| 7.7 | 20 | iPrOH | 99.9 | 98.5:1.5 |
| 7.8 | 20 | CH$_2$Cl$_2$ | 94.5 | 97.0:3.0 |
| 7.9 b) | 20 | EtOH | 99.8 | 99.0:1.0 |
| 7.10 c) | 20 | EtOH | 99.8 | 99.1:0.9 |
| 7.11 d) | 20 | EtOH | 99.9 | 99.0:1.0 |

For a) Reaction time 4 h; b) 200 mg substrate in 4 ml of ethanol; c) 600 mg substrate in 2 ml of ethanol; d) Catalyst prepared in situ by stirring 2.56 mg of [Ru(COD)(TFA)$_2$]$_2$ and 4.0 mg (S)-BINAP in a glove box in 3 ml of ethanol for 3 h at 50° C.

Example 8

(R)-tert-butyl 4-(5-methyl-7-oxo-5,6-dihydro-5H-cyclopenta[d]pyrimidin-4-yl)piperazine-1-carboxylate

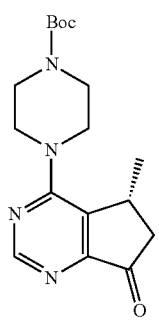 [SMILES: C[C@@H]1CC(=O)c2ncnc(N3CCN(C(=O)OC(C)(C)C)CC3)c21]

(R)-methyl 3-(4,6-dichloropyrimidin-5-yl)butanoate

Into a mixture of (R)-methyl 3-(4,6-dihydroxypyrimidin-5-yl)butanoate (1.00 kg, 4.70 mol), toluene (4.00 L), and 2,6-lutidine (0.550 L, 4.70 mol) was added phosphorous oxychloride (0.960 L, 10.6 mol) at 50° C. slowly. The mixture was stirred at 70° C. for 24 h. The solution was cooled to 0° C. To the mixture was slowly added 20% aqueous sodium hydroxide (about 40.0 mol, 1.60 kg in 8.00 L H$_2$O) while maintaining the internal temperature below 30° C., to obtain a final pH value between 5 and 6. Ethyl acetate (2.50 L) was added, stirred for 0.5 h, and then the layers were separated. The aqueous phase was extracted with ethyl acetate (3×1.00 L). The organics were combined and washed with 1 N hydrochloric acid (2×2.50 L), and brine (2.50 L). The organic layers were combined and dried over sodium sulfate and filtered through a glass fiber filter. The solution was concentrated to about 3.00 mL/g, and diluted with acetonitrile to about 7.00 mL/g. The sequence was repeated two times to remove residue ethyl acetate and toluene (confirmed by $^1$H NMR analysis). The remaining crude solution was used directly for next step without further purification or isolation.

(R)-methyl 3-(4,6-diiodopyrimidin-5-yl)butanoate

Into a solution of (R)-methyl 3-(4,6-dichloropyrimidin-5-yl)butanoate (36.0 g, 145 mmol) in acetonitrile (540 mL) was added sodium iodide (152 g, 1.02 mol). The mixture was stirred at 25° C. for 30 min and then cooled to about 5° C. Methanesulfonic acid (9.41 mL, 1.00 equiv) was added over 5 min. The mixture was agitated at about 5° C. for 3 h. The reactor was cooled to about 5° C. and N,N-diisopropylethylamine (20.3 mL, 116 mmol) was added. The mixture was agitated for 1 h while warming the mixture to 20° C. Saturated sodium sulfite solution was added until no further color change was observed to remove the iodine. Water (540 mL) was added and the pH was adjusted to between about 5 and 7. The biphasic mixture was concentrated under reduced pressure at a temperature of less than 40° C. to remove acetonitrile. The aqueous suspension was filtered to give 48.8 g (78% yield) of off-white solid product.

(R)-tert-butyl 4-(6-iodo-5-(4-methoxy-4-oxobutan-2-yl)pyrimidin-4-yl)piperazine-1-carboxylate Into a solution of (R)-methyl 3-(4,6-diiodopyrimidin-5-yl)butanoate (212 g, 491 mmol) and Boc-piperazine (101 g, 540 mmol) in methanol (424 mL) was added N,N-diisopropylethylamine (94.3 mL, 540 mmol). The mixture was heated at 60° C. for 24 h. Methanol was distilled off under reduced pressure below 40° C. To the mixture was added 318 mL of tetrahydrofuran. The above solvent swap process was repeated twice. To the mixture were added 424 mL of tetrahydrofuran, 212 mL of saturated aqueous ammonium chloride, and 21.2 mL of water. The organic layer was washed with 212 mL (1.00 vol.) of saturated aqueous ammonium chloride. This tetrahydrofuran solution was used for next step without further purification (91% weight assay yield).

(R)-3-(4-(4-(tert-butoxycarbonyl)piperazin-1-yl)-6-iodo-pyrimidin-5-yl)butanoic acid Into a solution of (R)-tert-butyl 4-(6-iodo-5-(4-methoxy-4-oxobutan-2-yl)pyrimidin-4-yl)piperazine-1-carboxylate (219 g, 0.447 mol) in tetrahydrofuran (657 mL) was added a solution of lithium hydroxide monohydrate (56.2 g, 1.34 mol) in 329 mL of water at 25° C. The mixture was stirred at 25° C. for 5 h. The bottom aqueous layer was discarded. The mixture was acidified with 1 N hydrochloric acid at 5° C. to give a final pH value of between about 1 to 2. The layers were separated. The top layer was then extracted with isopropyl acetate (440 mL×3), combined with the bottom layer, and washed with water (220 mL×2). The solvent was distilled off at reduced pressure below 50° C. The residual isopropyl acetate was azeotroped off with heptane under reduced pressure below 50° C. Product gradually precipitated out and was filtered to give an off-white to light yellow powder (196 g, 84% yield).

(R)-tert-butyl 4-(6-iodo-5-(4-(methoxy(methyl)amino)-4-oxobutan-2-yl)pyrimidin-4-yl)piperazine-1-carboxylate Into a solution of (R)-3-(4-(4-(tert-butoxycarbonyl)piperazin-1-yl)-6-iodo-pyrimidin-5-yl)butanoic acid (100 g, 210 mmol) in tetrahydrofuran (700 mL) was added 1,1'-carbonyldiimidazole (40.9 g, 252 mmol) in portions. The reaction mixture was stirred at 20° C. for 1 h and cooled to 5° C. N,O-dimethylhydroxyamine hydrochloride (41.0 g, 420 mmol) was added in portions followed by N-methylmorpholine (6.94 mL, 63.0 mmol). The mixture was stirred at 5° C. for about 1 h, slowly warmed up to room temperature, and stirred for 24 h. Saturated aqueous ammonium chloride (500 mL) and water (150 mL) were added to get a clear phase separation. The organic layer was washed with saturated aqueous ammonium chloride (500 mL) and brine (200 mL). The residual water was azeotroped off to less than 500 ppm by co-evaporation with tetrahydrofuran. The product, as a solution in tetrahydrofuran was used for the next step without further purification or isolation (weight assay yield: >99%).

(R)-tert-butyl 4-(5-methyl-7-oxo-6,7-dihydro-5H-cyclopenta[d]pyrimidin-4-yl)piperazine-1-carboxylate A solution of (R)-tert-butyl 4-(6-iodo-5-(4-(methoxy(methyl)amino)-4-oxobutan-2-yl)pyrimidin-4-yl)piperazine-1-carboxylate (109 g, 210 mmol) in tetrahydrofuran (600 mL) was purged with nitrogen for 30 min. Isopropyl magnesium chloride solution (159 mL, 210 mmol, 1.32 M in tetrahydrofuran) was added dropwise at −15° C. The mixture was stirred at −10° C. for 1 h and slowly transferred into a cold 20 wt % aqueous ammonium chloride (600 mL) with stirring while maintaining the internal temperature below 10° C. The organic layer was then washed with saturated aqueous ammonium chloride (500 mL). Tetrahydrofuran was distilled off at reduced pressure below 40° C. Methyl tert-butyl ether (350 mL) was slowly added while maintaining the internal temperature between 35° C. and 40° C., followed by heptane (350 mL). The mixture was slowly cooled down to 20° C. and product gradually precipitated out during the process. The slurry was filtered and the cake was dried at 40° C. under vacuum to give a gray solid (52.3 g, 75% yield over two steps). $^1$H NMR (300 MHz, CDCl$_3$) δ 8.73 (s, 1H), 3.92-3.83 (m, 2H), 3.73-3.49 (m, 7H), 2.96 (dd, J=16.5, 7.2 Hz, 1H), 2.33 (dd, J=16.5, 1.8 Hz, 1H), 1.50 (s, 9H), 1.32 (d, J=6.9 Hz, 3H). HRMS calcd. For $C_{17}H_{25}N_4O_3$ [M+H]$^+$: 333.1921, found 333.1924.

Example 9 tert-butyl 4-[(5R,7R)-7-hydroxy-5-methyl-6,7-dihydrocyclopenta[d]pyrimidin-4-yl]piperazine-1-carboxylate

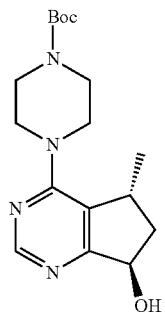 [SMILES: C[C@@H]1C[C@@H](O)c2ncnc(N3CCN(C(=O)OC(C)(C)C)CC3)c21]

A fade yellow suspension of 3 g tert-butyl 4-[(5R)-5-methyl-7-oxo-5,6-dihydrocyclopenta[d]pyrimidin-4-yl]piperazine-1-carboxylate in 21 ml aqueous buffer (100 mM 2-(N-morpholino)ethanesulfonic acid pH 5.8), 6 ml 2-Propanol and 3 mg oxidized cofactor NADP [Roche] formed under vigorous stirring. The reaction solution was heated to 40° C. and stirred for 5 min. and subsequently, the reduction started by the addition of 30 mg KRED-X1-P1B06. The pH was adjusted from 5.6 to 5.8. During the course of the reaction at 40° C. within 21.5 h achieving nearly complete conversion (IPC: 0.6 area % of educt) the pH increased to 6.4. Into the reaction 30 ml iso-propyl acetate was added and stirred vigorously for 15 min. The phase split occurred spontaneously. The separated water phase was twice extracted with 50 ml iso-propyl acetate, total 100 ml iso-propyl acetate. The combined organic phases were dried over MgSO$_4$, filtrated and evaporated under vacuum at 50° C. yielding in 3.07 g (102%) light red foam as crude product of the title compound containing around 4% isopropyl acetate. GC-EI-MS: 334.2 (M+H)$^+$; chiral HPLC: 99.88% (R,R), 0.12% (R,S) [254 nm; Chiralpak IC-3; 150*4.6 mm, 3 μm, flow 0.8 ml, 30° C., A: 60% n-heptane, B: 40% EtOH+0.1 DEA, 0-15 min 100% B, 15-17 min 100% B, 17.1 min 40% B]; chemical purity HPLC: 99.2 area % (contains 0.6 area % of educt). $^1$H NMR (600 MHz, CDCl$_3$) δ ppm 1.17-1.22 (m, 3H) 1.45-1.51 (m, 9H) 2.02 (s, 1H) 2.12-2.24 (m, 2H) 3.43-3.83 (m, 9H) 3.85-4.08 (m, 1H) 5.12 (t, J=7.2 Hz, 1H) 8.53 (s, 1H) (contains ~4% iso-propyl acetate).

Example 10.1-10.6

Tert-butyl 4-[(5R,7R)-7-hydroxy-5-methyl-6,7-dihydrocyclopenta yl]piperazine-1-carboxylate For examples 9.1-9.6, the procedure of Example 9 was repeated but the cofactor (NADP [Roche]) ratio was varied as indicated in the table below and a different ketoreductase variant was applied, namely KRED-X1 was applied.

TABLE 4

| Example | NADP | Reaction time | Substrate | Product |
|---------|------|---------------|-----------|---------|
| 9.1 | 100 | 16.5 | 0.8 | 2.8:96.4 |
| 9.2 | 200 | 21 | 0.7 | 1.9:97.4 |
| 9.3 | 400 | 22.5 | 0.6 | 1.7:97.7 |
| 9.4 | 1000 | 19.5 | 1.0 | 1.7:97.3 |
| 9.5 | 2000 | 16 | 3.0 | 1.5:95.5 |
| 9.6 | 3000 | 16 | 6.2 | 1.3:92.4 |

Example 11

Tert-butyl 4-[(5R,7R)-7-hydroxy-5-methyl-6,7-dihydrocyclopenta[d]pyrimidin-4-yl]piperazine-1-carboxylate A fade yellow suspension of 6 g tert-butyl 4-[(5R)-5-methyl-7-oxo-5,6-dihydrocyclopenta[d]pyrimidin-4-yl]piperazine-1-carboxylate in 18 ml aqueous buffer (100 mM 2-(N-morpholino)ethanesulfonic acid pH 5.8), 6 ml 2-Propanol and 6 mg oxidized cofactor NADP [Roche] was formed under vigorous stirring. The reaction solution was heated to 40° C. and stirred for 5 min. and subsequently, the reduction started by the addition of 60 mg KRED-X1-P1B06. The pH was adjusted from 5.5 to 5.8. During the course of the reaction at 40° C. within 2 d achieving nearly complete conversion (IPC: 1 d 1.3 area % educt, 2 d 1.2 area % educt) the pH increased to 6.0. Into the reaction 30 ml iso-propyl acetate was added and stirred vigorously for 15 min. The phase split occurred spontaneously. The separated water phase was twice extracted with 50 ml iso-propyl acetate, total 100 ml iso-propyl acetate. The combined organic phases were dried over $MgSO_4$, filtrated and evaporated under vacuum at 50° C. yielding in 6.02 g (99.7%) light red foam as crude product of the title compound containing around 4% isopropyl acetate. GC-EI-MS: 334.2 $(M+H)^+$; chiral HPLC: 99.88% (R,R), 0.12% (R,S) [254 nm; Chirapakl IC-3; 150*4.6 mm, 3 µm, flow 0.8 ml, 30° C., A: 60% n-heptane, B: 40% EtOH+0.1 DEA, 0-15 min 100% B, 15-17 min 100% B, 17.1 min 40% B]; chemical purity HPLC: 98.4 area % (contains 1.3 area % educt). $^1$H NMR (600 MHz, $CDCl_3$) δ ppm 1.2 (d, J=7.1 Hz 3H) 1.49 (s, 9H) 2.14-2.23 (m, 2H) 3.46-3.59 (m, 5H) 3.64 (ddd, J=13.1, 6.9, 3.3 Hz, 2H) 3.78 (ddd J=13.1, 7.2, 3.3 Hz, 2H) 5.12 (t, J=7.2 Hz, 1H) 8.53 (s, 1H) (contains ~4% iso-propyl acetate).

Example 12

Tert-butyl 4-[(5R,7R)-7-hydroxy-5-methyl-6,7-dihydrocyclopenta[d]pyrimidin-4-yl]piperazine-1-carboxylate A fade yellow suspension of 3 g tert-butyl 4-[(5R)-5-methyl-7-oxo-5,6-dihydrocyclopenta[d]pyrimidin-4-yl]piperazine-1-carboxylate in 21 ml aqueous buffer (100 mM Potassium dihydrogen phosphate pH 7.2; 2 mM Magnesium chloride), 6 ml 2-Propanol and 3 mg oxidized cofactor NADP [Roche] formed under vigorous stirring. The reaction solution was heated to 40° C. and stirred for 5 min. and subsequently, the reduction started by the addition of 30 mg KRED-X1-P1B06. The pH was adjusted from 7.5 to 7.2. During the course of the reaction at 40° C. within 18.5 h achieving nearly complete conversion (IPC: 0.8 area % educt) the pH decreased to 7.15. Into the reaction 30 ml iso-propyl acetate was added and stirred vigorously for 15 min. The phase split occurred spontaneously. The separated water phase was twice extracted with 50 ml iso-propyl acetate, total 100 ml iso-propyl acetate. The combined organic phases were dried over $MgSO_4$, filtrated and evaporated under vacuum at 50° C. yielding in 3.06 g (102%) light red foam as crude product of the title compound containing around 4% isopropyl acetate. GC-EI-MS: 334.2 $(M+H)^+$; chiral HPLC: 99.76% (R,R), 0.24% (R,S) [254 nm; Chirapakl IC-3; 150*4.6 mm, 3 µm, flow 0.8 ml, 30° C., A: 60% n-heptane, B: 40% EtOH+0.1 DEA, 0-15 min 100% B, 15-17 min 100% B, 17.1 min 40% B]; chemical purity HPLC: 98.9 area % (contains 0.8 area % educt). $^1$H NMR (600 MHz, $CDCl_3$) δ ppm 1.16-1.22 (m, 3H) 1.45-1.53 (m, 9H) 2.12-2.25 (m, 2H) 3.42-3.86 (m, 9H) 4.13 (br. s., 1H) 5.12 (t, J=7.2 Hz, 1H) 8.44-8.59 (m, 1H) (contains ~4% iso-propyl acetate).

Example 13.1-13.7

Tert-butyl 4-[(5R,7R)-7-hydroxy-5-methyl-6,7-dihydrocyclopenta[d]pyrimidin-4-yl]piperazine-1-carboxylate 10 mg tert-butyl 4-[(5R)-5-methyl-7-oxo-5,6-dihydrocyclopenta[d]pyrimidin-4-yl]piperazine-1-carboxylate dissolved in a mixture of 500 DMSO and 50 µl 2-Propanol was added into each well of a deep well plate containing 300 µl buffer (MES 100 mM, $MgCl_2$ 2 mM; pH 5.8) 1 mg NADP and variants of KRED-X1. After shaking for 1.5 h at room temperature into each well 0.5 ml MeOH was added and analyzed by HPLC. The results of the best variants are listed in the table below.

TABLE 5

| Example | Ketoreductase Variant | Product (R,S):(R,R) |
|---------|----------------------|---------------------|
| 13.1 | KRED-X1.1-P1F01 | 0.00:85:96 |
| 13.2 | KRED-X1.1-P1H10 | 0.00:81.87 |
| 13.3 | KRED-X1.1-P1C08 | 0.00:78.20 |
| 13.4 | KRED-X1.1-P1C04 | 0.03:94.83 |
| 13.5 | KRED-X1.1-P1G11 | 0.03:94.06 |
| 13.6 | KRED-X1.1-P1C11 | 0.04:86.69 |
| 13.7 | KRED-X1-P1B06 | 0.08:79.80 |

Example 13a

Tert-butyl 4-[(5R,7R)-7-hydroxy-5-methyl-6,7-dihydrocyclopenta[d]pyrimidin-4-yl]piperazine-1-carboxylate A suspension of 50 g (150 mmol) tert-butyl 4-[(5R)-5-methyl-7-oxo-5,6-dihydrocyclopenta[d]-pyrimidin-4-yl] piperazine-1-carboxylate in 100 ml aqueous buffer (100 mM Potassium dihydrogen phosphate pH 7.2), 78 g 2-Propanol and 50 mg NAD (75 µmol) was formed under vigorous stirring. The reduction started by the addition of 500 mg KRED-X1.1-P1F01. The reaction mixture is sparged with nitrogen and heated to 40° C. for 22 hours. After reaction completion 174 g isopropylacetate are added, agitated, phases were split and the aqueous phase removed. The aqueous phase was extracted again with 174 g isopropylacetate. The aqueous phase was removed and the organic phases were combined and concentrated at 35° C. in vacuo to a final volume of 115 mL. At the same temperature 212 g Heptane are added within 1 hour, the suspension is aged for 1 hour and cooled to 10° C. within 6 hours. The suspension is filtered and washed with 68 g heptane. After drying of the filter cake for 4 hours at 50° C. and 41.1 g (82% yield, purity 100% area) white crystals are obtained.

Example 13b

Tert-butyl 4-[(5R,7R)-7-hydroxy-5-methyl-6,7-dihydrocyclopenta[d]pyrimidin-4-yl]piperazine-1-carboxylate A suspension of 40 g (150 mmol) tert-butyl 4-[(5R)-5-methyl-7-oxo-5,6-dihydrocyclopenta[d]-pyrimidin-4-yl] piperazine-1-carboxylate in 240 ml aqueous buffer (containing 3.3 g KH₂PO₄ and 8.4 g K₂HPO₄), 26 g Glucose and 40 mg NAD was formed under vigorous stirring. The reduction warmed to 35° C. and started by the addition of 400 mg KRED-X1.1-P1F01 and 400 mg GDH-101. Over the course of the reaction (26 hours) the pH is kept at 7.0 using 58.8 mL aq. KOH (10% (m/m)). After reaction completion 290 g isopropylacetate and 117 g NaSCN are added, agitated, phases were split and the aqueous phase removed. The organic phase is washed with 200 g water and filtered using a filtrox filter plate, the aqueous phase washed with 175 g isopropylacetate. The combined organic phases are concentrated at 25° C. in vacuo to a final volume of 100 mL. At 25° C. 383 g Heptane are added and within 1 hour. The suspension is cooled to 0° C. within 30 minutes and aged for 30 minutes, The suspension is filtered and washed with 91 g heptane. After drying of the filter cake for 16 hours at 50° C. and 30.9 g (76% yield, purity 100% area) white crystals are obtained.

Example 14 tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate

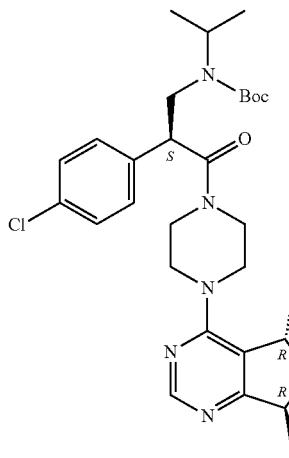

To a three-neck 500 mL reactor, equipped with a mechanical stirrer, a nitrogen inlet, and a thermometer was charged tert-butyl 4-((5R,7R)-7-hydroxy-5-methyl-6,7-dihydro-5H-cyclopenta[d]pyrimidin-4-yl)piperazine-1-carboxylate (16.7 g, 52.5 mmol) and 2-propanol (65 mL). The solution was heated to 55° C. Then 20.8% (m/m) HCl in 2-propanol (24.6 g, 140 mmol) was added within 10 minutes at 55° C. The suspension was stirred until reaction completion. The reaction mixture was cooled to 10° C. and 4-methylmorpholine (32.9 g, 325 mmol) were added. The mixture was stirred at 15° C. for 30 min. (S)-3-((tert-butoxycarbonyl)(isopropyl) amino)-2-(4-chlorophenyl)propanoic acid sodium salt (19.1 g, 52.5 mmol) and 2-propanol (73 g) were added and the reaction mixture was cooled to 5° C. Propane phosphonic anhydride (T3P) (50 w % (m/m) in toluene) (35 g, 57.3 mmol) was added at a rate maintaining the temperature at 5° C.

Upon reaction completion, 20 g water were added. The solution was concentrated by distillation at 45° C. and 150 mbar until a final volume of 100 mL. Toluene (260 g) was added. The solution was again concentrated by distillation at 45° C. and 150 mbar until a final volume of 300 mL. Water (150 g) was added and the suspension was stirred for 15 minutes. The phases were separated for 15 minutes and the aqueous phase was removed. Water (100 g) was added and the suspension was stirred for 15 minutes. The phases were separated for 15 minutes and the aqueous phase was removed. Again water (100 g) was added and the suspension was stirred for 15 minutes. The phases were separated for 15 minutes and the aqueous phase was removed. The solution was concentrated by distillation at 45° C. and 150 mbar until a final volume of 100 mL. n-Heptane (34 g) was added, the solution was cooled to 0° C. within 1 hour to allow tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate to crystallize. Further n-Heptane (170 g) was added. The suspension was aged for 2 hours, filtered and washed with a mixture of toluene (6.4 g) and n-heptane (29.2 g) followed twice by heptane (each 68.4 g). The filter cake was dried at ≤55° C. to give tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate as an off-white solid, isolated 23.9 g, 86% yield. ($^1$H NMR (600 MHz, CDCl₃) δ ppm 0.68 (br. s., 3H) 0.94-1.08 (m, 3H) 1.14 (d, J=7.0 Hz, 3H) 1.47 (s, 10H) 2.06-2.27 (m, 2H) 3.30 (br. s., 1H) 3.38-3.53 (m, 5H) 3.56-3.73 (m, 4H) 3.78 (br. s., 3H) 4.62 (br. s., 1H) 5.10 (t, J=7.1 Hz, 1H) 7.24 (s, 1H) 8.49 (s, 1H).

Example 15

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride

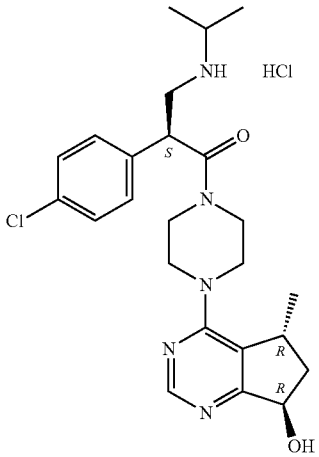

To a 500 mL reactor, equipped with a mechanical stirrer, a nitrogen inlet, a thermometer and a pH-meter was added tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (50 g) and 2-propanol (128 g). The solution was heated to 50° C. A solution of HCl in 2-propanol (21% wt (m/m), 46.7 g) was added at 50° C. The solution was maintained at 50° C. until reaction completion and the mixture was cooled to 25° C. Ammonia solution in 2-propanol (2M, 66.6 g, 1.66 eq) was added within approx. 1 hour until pH 6.7 was reached. The suspension was cooled to 0° C. and filtered. The cake was washed with 2-propanol (39 g). The filtrate was concentrated by distillation at 50° C. and 150 mbar until a final volume of 100 mL. Ethyl acetate (130 g) was added to the solution. The slurry was solvent-switched at 40° C. at constant volume (300 mL) using ethyl acetate (670 g). The suspension was cooled to 5° C. and the slurry filtered. The filter cake was washed with EtOAc (105 mL) and dried under vacuum at 100° C. for 16 hours to afford (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride as an off-white solid: 36.4 g (82% yield). ($^1$H NMR (600 MHz, D$_2$O) δ ppm 0.92 (d, J=7.1 Hz, 3H) 1.23 (t, J=6.4 Hz, 6H) 1.89-2.15 (m, 2H) 2.85-3.06 (m, 1H) 3.17-3.59 (m, 10H) 3.83 (d, J=10.5 Hz, 2H) 4.33 (dd, J=8.5, 4.9 Hz, 1H) 4.98 (t, J=7.0 Hz, 1H) 7.23 (d, J=8.5 Hz, 2H) 7.36 (d, J=8.7 Hz, 2H) 8.10-8.35 (m, 1H). LCMS [M+H]$^+$ 458.2).

Example 16

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride To a 500 mL reactor, equipped with a mechanical stirrer, a nitrogen inlet, a thermometer and a pH-meter was added tert-butyl ((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)(isopropyl)carbamate (50 g) and 1-propanol (131 g). The solution was heated to 60° C. A solution of HCl in 1-propanol (22% wt (m/m), 38.0 g) was added at 60° C. The solution was maintained at 50° C. until reaction completion and the mixture was cooled to 25° C. Aq. NaOH (28%) (16 g) was added until pH 6 was reached. The suspension was concentrated at 60° C. in vacuo until a final volume of 100 mL is reached. The suspension is cooled to 20° C., 90 g ethyl acetate are added and filtered with a filtrox plate. Reactor and filter unit are washed with 41 g 1-propanol/ethyl acetate. The solution is filtered at 20° C. through charcoal filter pads, the reactor and filter is rinsed with 82 g 1-propanol/ethyl acetate. At 60° C. the solution is concentrated in vacuo until a final volume of 300 mL. The distillation is continued at 60° C. and simultaneously 1260 g ethyl acetate are added keeping the volume constant.

The suspension was cooled to 5° C. and the slurry filtered. The filter cake was washed with EtOAc (105 mL) and dried under vacuum at 60° C. for 16 hours to afford (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one monohydrochloride as an off-white solid: 36.5 g (81% yield, 91.4% (m/m) purity, 99.9% (area) assay).

The invention claimed is:
1. A process for the manufacture of compounds of formula (III)

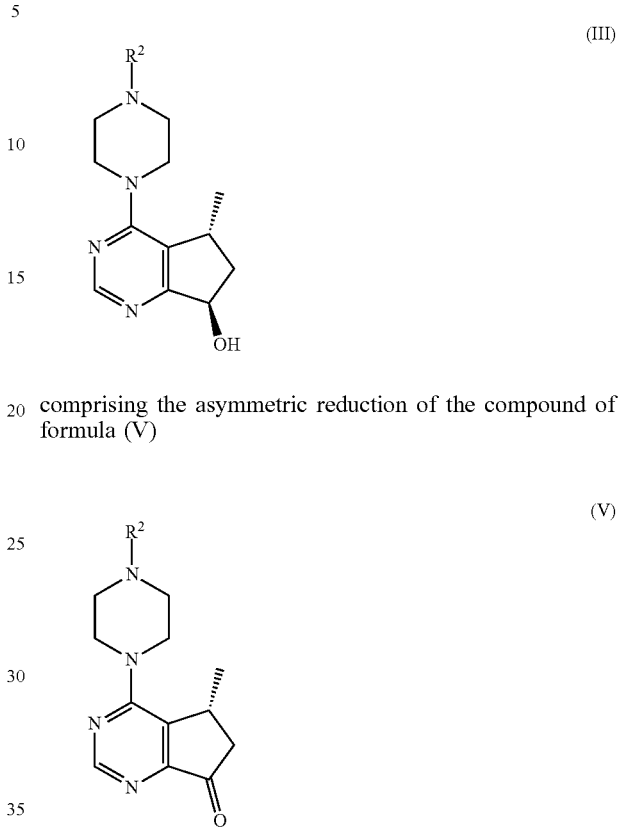

comprising the asymmetric reduction of the compound of formula (V)

catalyzed by an oxidoreductase, selected from the group consisting of KRED-X1.1.P1B06, and KRED-X1.1-P1F01, or a variant thereof, in the presence of a cofactor using a substrate coupled cofactor regeneration system with 2-propanol as final reductant in the absence of glucose dehydrogenase (GDH) wherein:
R$^2$ is an amino-protecting group selected from the group consisting of benzyl, benzyloxycarbonyl (carbobenzyloxy, CBZ), 9-Fluorenylmethyloxycarbonyl (Fmoc), p-methoxybenzyloxycarbonyl, p-nitrobenzyloxycarbonyl, tert-butoxycarbonyl (BOC), and trifluoroacetyl.
2. The process according to claim 1, wherein the oxidoreductase catalyzes the asymmetric reduction of a compound of formula (V) to a compound of formula (III) with a diastereoselectivity of at least 99% diastereomeric excess (de).
3. The process according to claim 1, wherein the oxidoreductase catalyzes the asymmetric reduction of a compound of formula (V) to a compound of formula (III) with a diastereoselectivity of at least at least 98% de.
4. The process according to claim 1, wherein the cofactor which is oxidized in the asymmetric reduction of a compound of formula (V) to a compound of formula (III) is NADH or NADPH.
5. The process according to claim 1, wherein the catalysis further comprises continuous removal of acetone formed by the coupled cofactor regeneration-system.
6. The process according to claim 1, wherein the asymmetric reduction of a compound of formula (V) to a compound of formula (III) is performed in an aqueous medium in the presence of one or more organic cosolvents.

7. The process according to claim 6, wherein the organic cosolvents are present in a total concentration from 1 to 50% V.

8. The process according to claim 6, wherein the organic cosolvents are present in a total concentration from 5 to 30% V.

9. The process according to claim 6, wherein the organic cosolvent is 2-propanol.

10. The process according to claim 1, wherein the asymmetric reduction of a compound of formula (V) to a compound of formula (III) is performed in an aqueous buffer.

11. The process according to claim 10, wherein the buffer is 2-(N-morpholino)ethanesulfonic acid (MES) or potassium dihydrogen phosphate (PBS).

12. The process according to claim 1, wherein the asymmetric reduction of a compound of formula (V) to a compound of formula (III) is performed at a reaction temperature between 20° C. and 45° C.

* * * * *